US012560617B2

(12) United States Patent
Britz-McKibbin et al.

(10) Patent No.: US 12,560,617 B2
(45) Date of Patent: Feb. 24, 2026

(54) METHOD OF DIAGNOSING AND TREATMENT MONITORING OF CROHN'S DISEASE AND ULCERATIVE COLITIS

(71) Applicant: McMaster University, Hamilton (CA)

(72) Inventors: Philip Britz-McKibbin, Hamilton (CA); Nikhil Pai, Hamilton (CA)

(73) Assignee: McMaster University, Ontario (CA)

( * ) Notice: Subject to any disclaimer, the term of this patent is extended or adjusted under 35 U.S.C. 154(b) by 927 days.

(21) Appl. No.: 17/784,979

(22) PCT Filed: Dec. 13, 2020

(86) PCT No.: PCT/CA2020/051717

§ 371 (c)(1),
(2) Date: Jun. 13, 2022

(87) PCT Pub. No.: WO2021/113989

PCT Pub. Date: Jun. 17, 2021

(65) Prior Publication Data

US 2023/0015257 A1     Jan. 19, 2023

Related U.S. Application Data

(60) Provisional application No. 62/947,987, filed on Dec. 13, 2019.

(51) Int. Cl.
G01N 33/68     (2006.01)
(52) U.S. Cl.
CPC ..... G01N 33/6893 (2013.01); G01N 33/6848 (2013.01); G01N 2800/065 (2013.01)

(58) Field of Classification Search
USPC ........................................................ 436/173
See application file for complete search history.

(56) References Cited

FOREIGN PATENT DOCUMENTS

WO     2011041892     4/2011

OTHER PUBLICATIONS

Yamamoto, Mai et al. Metabolomics Offers New Insights into Pediatric Inflammatory Bowel Disease for Non-invasive Diagnosis of Crohn's Disease and Ulcerative Colitis. Publication Pending.
Thibault, Ronan, et al. "Down-regulation of the monocarboxylate transporter 1 is involved in butyrate deficiency during intestinal inflammation." Gastroenterology 133.6 (2007): 1916-1927.
Duboc, Henri, et al. "Connecting dysbiosis, bile-acid dysmetabolism and gut inflammation in inflammatory bowel diseases." Gut 62.4 (2013): 531-539.

(Continued)

*Primary Examiner* — Xiaoyun R Xu
(74) *Attorney, Agent, or Firm* — Gowling WLG (Canada) LLP

(57)     ABSTRACT

Methods of diagnosing Crohn's disease and ulcerative colitis in subjects is provided based on the determination of metabolites in urine samples, such as serine, hypoxanthine, kynurenine, threonine, dimethylglycine, tryptophan, indoxylsulfate, phenylacetylglutamine, sialic acid, 5-hydroxy-6-indolyl-o-sulfate, 5-($\Delta$-carboxybutyl) homocysteine, and/or an anion having m/z:RMT:polarity of 345.1553:0.770:n, or determination of metabolites in stool samples, such as ketodeoxycholic acid, cholic acid, choline, tryptophan, trimethyllysine, serine, butyric acid, lactic acid, hypoxanthine and/or guanine.

11 Claims, 17 Drawing Sheets

(56)                    References Cited

OTHER PUBLICATIONS

Scoville, Elizabeth A., et al. "Alterations in lipid, amino acid, and energy metabolism distinguish Crohn's disease from ulcerative colitis and control subjects by serum metabolomic profiling." Metabolomics 14.1 (2018): 1-12.

Lu, Kun, et al. "Serum metabolomics in a Helicobacter hepaticus mouse model of inflammatory bowel disease reveal important changes in the microbiome, serum peptides, and intermediary metabolism." Journal of proteome research 11.10 (2012): 4916-4926.

Balasubramanian, Krithika, et al. "Metabolism of the colonic mucosa in patients with inflammatory bowel diseases: an in vitro proton magnetic resonance spectroscopy study." Magnetic resonance imaging 27.1 (2009): 79-86.

Schicho, Rudolf, et al. "Quantitative metabolomic profiling of serum, plasma, and urine by 1H Nmr spectroscopy discriminates between patients with inflammatory bowel disease and healthy individuals." Journal of proteome research 11.6 (2012): 3344-3357.

Stephens, Natasha S., et al. "Urinary NMR metabolomic profiles discriminate inflammatory bowel disease from healthy." Journal of Crohn's and Colitis 7.2 (2013): e42-e48.

Kolho, Kaija-Leena, et al. "Faecal and serum metabolomics in paediatric inflammatory bowel disease." Journal of Crohn's and Colitis 11.3 (2017): 321-334.

Marchesi, Julian R., et al. "Rapid and noninvasive metabonomic characterization of inflammatory bowel disease." Journal of proteome research 6.2 (2007): 546-551.

Williams, Horace RT, et al. "Characterization of inflammatory bowel disease with urinary metabolic profiling." Official journal of the American College of Gastroenterology| ACG 104.6 (2009): 1435-1444.

De Preter, Vicky. "Metabolomics in the clinical diagnosis of inflammatory bowel disease." Digestive Diseases 33.Suppl. 1 (2015): 2-10.

Bjerrum, Jacob Tveiten, et al. "Metabonomics of human fecal extracts characterize ulcerative colitis, Crohn's disease and healthy individuals." Metabolomics 11.1 (2015): 122-133.

Alonso, Arnald, et al. "Urine metabolome profiling of immune-mediated inflammatory diseases." Bmc Medicine 14.1 (2016): 1-12.

Green, Nicole, et al. "A review of dietary therapy for IBD and a vision for the future." Nutrients 11.5 (2019): 947.

Search Report for PCT/CA2020/051717.

Written Opinion for PCT/CA2020/051717.

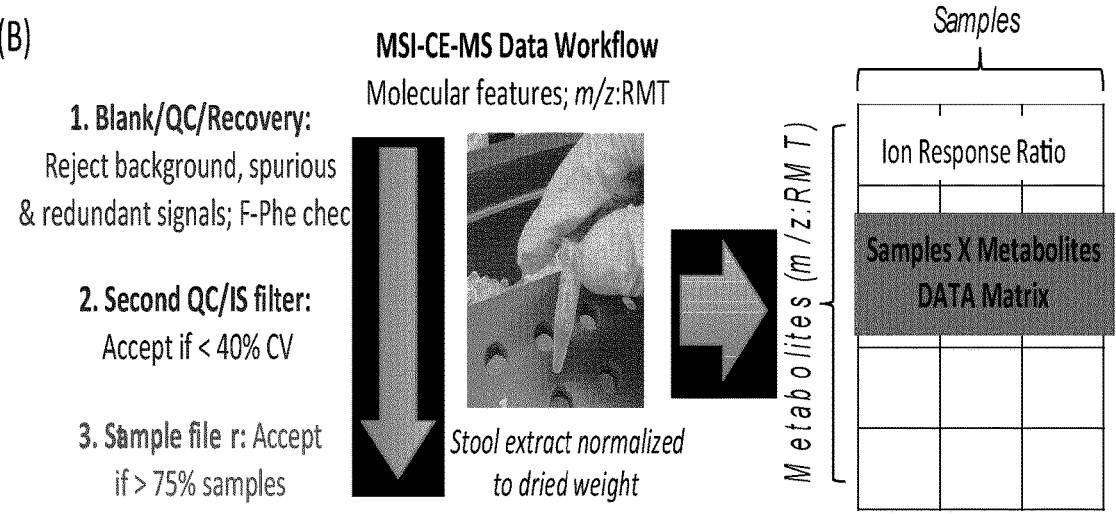

1. Blank/QC/Recovery:
Reject background, spurious & redundant signals; F-Phe chec

2. Second QC/IS filter:
Accept if < 40% CV

3. Sample file r: Accept
if > 75% samples

MSI-CE-MS Data Workflow
Molecular features; *m/z*:RMT

*Stool extract normalized to dried weight*

*Samples*

Ion Response Ratio

Samples X Metabolites DATA Matrix

*Metabolites (m/z:RMT)*

*Authenticated Metabolites: Curated List of Unique, Reproducible & Representative Sample-derived Metabolites*

(C) Control Chart for Recovery Standard in Stool Extracts by MSI-CE-MS

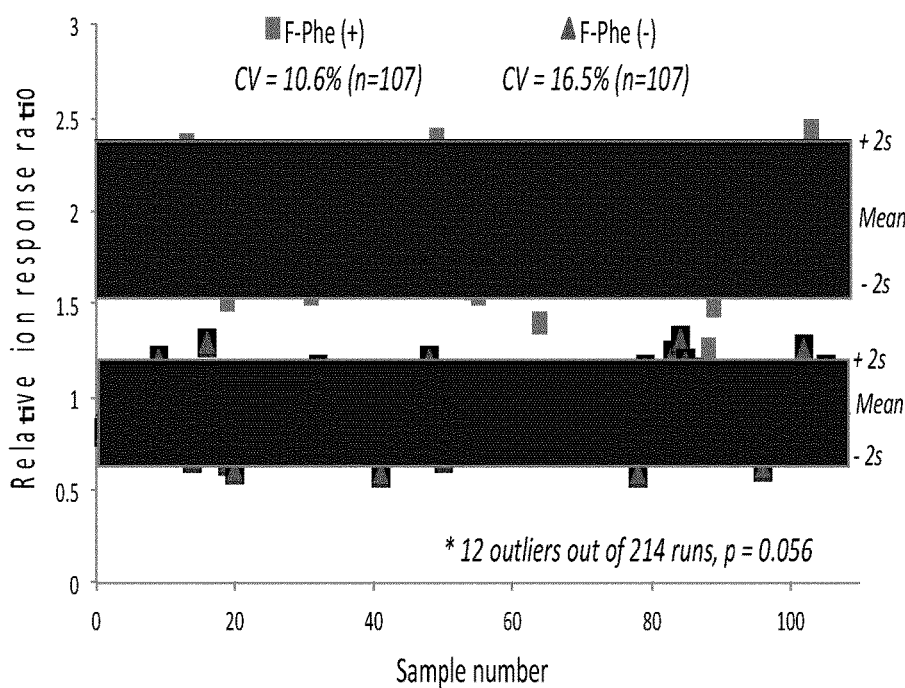

F-Phe (+)
CV = 10.6% (n=107)

F-Phe (-)
CV = 16.5% (n=107)

* 12 outliers out of 214 runs, p = 0.056

Relative ion response ratio

Sample number

FIG. 5

Top-ranked ratiometric biomarkers identified by MSI-CE-MS that differentiate pediatric CD from UC in osmolality normalized urine.

| Ratiometric Biomarkers | p-value | FC | Effect size | q-value |
|---|---|---|---|---|
| Serine/Indoxylsulfate | 1.71 E-05 | 0.18 | 0.73 | 1.86 E-03 |
| Threonine/Phenylacetylglutamine | 2.70 E-05 | 0.24 | 0.72 | 1.86 E-03 |
| Serine/Hydroxyindole sulfate | 4.05 E-05 | 0.19 | 0.71 | 1.86 E-03 |
| Kynurenine/Indoxylsulfate | 1.23 E-04 | 0.08 | 0.67 | 3.90 E-03 |
| Serine/Phenylacetylglutamine | 1.69 E-04 | 0.37 | 0.66 | 3.90 E-03 |
| Threonine/Hydroxyindole sulfate | 1.69 E-04 | 0.10 | 0.66 | 3.90 E-03 |
| Threonine/Indoxylsulfate | 2.32 E-04 | 0.09 | 0.65 | 4.58 E-03 |
| Tryptophan /Indoxylsulfate | 7.16 E-04 | 0.32 | 0.61 | 9.88 E-03 |
| Kynurenine/Hydroxyindole sulfate | 9.23 E-04 | 0.11 | 0.60 | 0.0106 |
| Tryptophan/Hydroxyindole sulfate | 1.50 E-03 | 0.28 | 0.58 | > 0.05 |

*\* Statistical significance calculated by a Mann-Whitney U-test, p < 0.05, whereas q-value is based on Benjamini-Hochberg FDR; Abbreviation: FC = median fold-change*

FIG. 7

Summary of 104 stool metabolites measured in samples of pediatric IBD patients with $m/z$, RMT, ionization mode (p = ESI positive ion mode, n = ESI negative ion mode), molecular formula, chemical ID or tentative ID, confidence level of the ID and chemical classification based on Human Metabolome Database (HMDB). Column "common" indicates the common metabolites found in both urine and stool metabolite (1 = commonly found, 0 = not found in urine).

| $m.z$:RMT:mode | Chemical ID | Molecular Formula | Metabolite Class | Confirmed level | Common |
|---|---|---|---|---|---|
| 87.0452:1.054:n | Butyric acid [a] | C4H8O2 | organic acid | 1 | 1 |
| 88.0404:1.005:n | Sarcosine | C3H7NO2 | amino acid | 3 | 0 |
| 89.0244:1.1400:n | Lactic acid | C3H6O3 | organic acid | 1 | 1 |
| 101.0608:0.99:n | Ethylmethylacetic acid [a] | C5H10O2 | organic acid | 3 | 0 |
| 117.0193:1.844:n | Succinic acid | C4H6O4 | organic acid | 1 | 1 |
| 117.0555:0.989:n | 2-Methyl-3-hydroxybutyric or 3-Hydroxyisovaleric acid | C5H10O3 | organic acid | 3 | 0 |
| 133.0142:1.862:n | Malic acid | C4H6O5 | organic acid | 1 | 0 |
| 145.0514:1.456:n | 2-Methylglutaric acid [a] | C6H10O4 | organic acid | 2 | 1 |
| 146.0459:0.956:n | Glutamic acid | C5H9NO4 | amino acid | 1 | 0 |
| 147.0299:1.618:n | 2-Hydroxyglutaric acid | C5H8O5 | organic acid | 2 | 0 |
| 149.0608:0.943:n | Hydrocinnamic acid or phenylpropanoic acid [a] | C9H10O2 | organic acid | 3 | 0 |
| 167.0201:0.962:n | Uric acid | C5H4N4O3 | organic acid | 1 | 1 |
| 178.051:0.911:n | Hippuric acid [a] | C9H9NO3 | organic acid | 1 | 1 |
| 182.0459:0.942:n | 4-Pyridoxic acid | C8H9NO4 | organic acid | 1 | 1 |
| 187.0071:1.059:n | p-Cresol sulfate | C7H8O4S | phenylsulfate | 1 | 1 |
| 188.0558:1.354:n | N-Acetylglutamate | C7H11NO5 | amino acid | 3 | 1 |
| 218.1034:0.832:n | Pantothenic acid | C9H17NO5 | organonitrogen | 1 | 1 |
| 308.0987:0.788:n | N-Acetylneuraminic acid | C11H19NO9 | amino sugar | 1 | 1 |
| 391.2865:0.755:n | Deoxycholic acid [a] | C24H40O4 | steroid | 1 | 0 |
| 405.2646:0.753:n | 7-Ketodeoxycholic acid [a] | C24H38O5 | steroid | 3 | 0 |
| 407.2803:0.748:n | Cholic acid | C24H40O5 | steroid | 1 | 1 |
| 448.3068:0.739:n | Deoxycholic acid glycine conjugate | C26H43NO5 | steroid | 1 | 0 |
| 464.3018:0.736:n | Glycocholic acid | C26H43NO6 | steroid | 1 | 0 |
| 471.2422:0.993:n | Chenodeoxycholic acid 3-sulfate [a] | C24H40O7S | steroid | 2 | 0 |
| 498.2895:0.741:n | Taurodeoxycholic acid [a] | C26H45NO6S | steroid | 1 | 0 |
| 514.2844:0.738:n | Taurocholic acid | C26H45NO7S | steroid | 1 | 0 |
| 76.0393:0.704:p | Glycine | C2H5NO2 | amino acid | 1 | 1 |
| 89.1079:0.402:p | Putrescine | C4H12N2 | amine | 1 | 0 |
| 90.055:0.747:p | Alanine | C3H7NO2 | amino acid | 1 | 1 |
| 103.1236:0.424:p | Cadaverine | C5H14N2 | amine | 1 | 0 |
| 104.0706:0.664:p | Gamma-aminobutyrate | C4H9NO2 | amino acid | 1 | 1 |
| 104.1069:0.560:p | Choline | C5H14NO | organonitrogen | 1 | 1 |
| 106.0499:0.844:p | Serine | C3H7NO3 | amino acid | 1 | 1 |

FIG. 7 continued

| | | | | | |
|---|---|---|---|---|---|
| 112.0875:0.410:p | Histamine | C5H9N3 | amine | 3 | 0 |
| 114.0662:0.646:p | Creatinine | C4H7N3O | amino acid | 1 | 1 |
| 116.0706:0.586:p | Proline | C5H9NO2 | amino acid | 1 | 0 |
| 116.0706:0.907:p | 4-Amino-2-methylenebutanoic acid | C5H9NO2 | amino acid | 3 | 0 |
| 118.0862:0.839:p | Betaine | C5H11NO2 | amino acid | 1 | 0 |
| 118.0862:0.690:p | Valine | C5H11NO2 | amino acid | 1 | 0 |
| 120.0652:0.887:p | Threonine | C4H9NO3 | amino acid | 1 | 1 |
| 124.0393:0.86:p | Picolinic acid [a] | C6H5NO2 | amino acid | 3 | 0 |
| 131.1179:0.745:p | Acetylputriscine | C6H14N2O | amine | 1 | 1 |
| 132.0768:0.768:p | Creatine | C4H9N3O2 | amino acid | 1 | 1 |
| 132.101:0.862:p | Isoleucine | C6H13NO2 | amino acid | 1 | 0 |
| 132.101:0.852:p | Leucine | C6H13NO2 | amino acid | 1 | 0 |
| 133.0969:0.586:p | Ornithine | C5H12N2O2 | amino acid | 1 | 1 |
| 134.0445:0.969:p | Aspartate | C4H7NO4 | amino acid | 1 | 0 |
| 137.0457:1.063:p | Hypoxanthine | C5H4N4O | purine | 1 | 1 |
| 138.055:0.892:p | Trigonelline [a] | C7H7NO2 | organic acid | 1 | 1 |
| 141.0659:0.698:p | Imidazole propionate | C6H8N2O2 | organic acid | 2 | 1 |
| 145.1329:0.733:p | Acetylcadaverine [a] | C7H16N2O | amine | 2 | 0 |
| 146.1175:0.671:p | Acetylcholine/4-Trimethylammonio butanoic acid | C7H16NO2 | organonitrogen | 3 | 0 |
| 147.0764:0.905:p | Glutamine | C5H10N2O3 | amino acid | 1 | 1 |
| 147.1128:0.566:p | Lysine | C6H14N2O2 | amino acid | 1 | 1 |
| 148.0598:0.918:p | Glutamate | C5H9NO4 | amino acid | 1 | 0 |
| 150.0583:0.897:p | Methionine | C5H11NO2S | amino acid | 1 | 1 |
| 152.0567:0.734:p | Guanine | C5H5N5O | purine | 1 | 0 |
| 152.0567:1.152:p | *Unknown* | C7H7N2O2 | NA | 4 | 0 |
| 156.0767:0.606:p | Histidine | C6H9N3O2 | amino acid | 1 | 1 |
| 160.1331:0.699:p | Aminooctanoic acid | C8H17NO2 | NA | 4 | 0 |
| 162.1125:0.742:p | Carnitine | C7H15NO3 | organonitrogen | 1 | 1 |
| 166.0723:0.716:p | Methylguanine | C6H7N5O | purine | 1 | 1 |
| 166.0863:0.921:p | Phenylalanine | C9H11NO2 | amino acid | 1 | 1 |
| 170.0924:0.643:p | 3-Methylhistidine | C7H11N3O2 | amino acid | 1 | 1 |
| 175.119:0.586:p | Arginine | C6H14N4O2 | amino acid | 1 | 0 |
| 176.0658:0.862:p | Acetyl-aspartic acid | C6H9NO5 | amino acid | 3 | 1 |
| 176.1029:0.938:p | Citrulline | C6H13N3O3 | amino acid | 1 | 0 |
| 182.0809:0.954:p | Tyrosine | C9H11NO3 | amino acid | 1 | 1 |
| 189.1234:0.837:p | Alpha-Acetyllysine/$N_6$-Acetyllysine | C8H16N2O3 | amino acid | 3 | 0 |
| 189.1598:0.612:p | Trimethyllysine | C9H20N2O2 | amino acid | 1 | 1 |
| 191.0668:0.998:p | Aspartyl-glycine [a] | C6H10N2O5 | amino acid | 3 | 1 |
| 198.0851:0.846:p | *Unknown* | C8H11N3O3 | NA | 4 | 0 |
| 204.123:0.792:p | Acetyl-carnitine | C9H17NO4 | organonitrogen | 1 | 1 |
| 205.0972:0.927:p | Tryptophan | C11H12N2O2 | amino acid | 1 | 1 |

FIG. 7 continued

| | | | | | |
|---|---|---|---|---|---|
| 231.1704:0.888:p | *Unknown* | C14H20N3 | NA | 4 | 0 |
| 241.0311:0.932:p | Cystine | C6H12N2O4S2 | amino acid | 1 | 1 |
| 243.1095:0.606:p | *Unknown* | C10H14N2O5 | NA | 4 | 0 |
| 247.0373:0.588:p | *Unknown* | C9H6N6OS | NA | 4 | 0 |
| 268.104:0.857:p | Deoxyguanosine | C10H13N5O4 | purine | 3 | 0 |
| 276.1559:0.637:p | *Unknown* | C14H19N4O2 | NA | 4 | 0 |
| 284.0989:1.151:p | Guanosine | C10H13N5O5 | purine | 2 | 0 |
| 287.2447:0.643:p | $N_1,N_{12}$-Diacetylspearmine | C14H30N4O2 | polyamine | 2 | 0 |
| 295.1288:0.936:p | Phenylalanyl-Glutamine | C14H19N3O4 | amino acid | 3 | 0 |
| 298.097:0.873:p | *Unknown* | C7H15N5O8 | NA | 4 | 0 |
| 298.097:0.617:p | Methylthioadenosine | C11H15N5O3S | purine | 2 | 1 |
| 308.5167:0.735:p | *Unknown* [a] | C21H41N | NA | 4 | 0 |
| 235.1178:0.994:n | *Unknown* [b] | C6H16N6O4 | NA | 4 | 0 |
| 632.2044:0.713:n | Sialyllactose [b] | C23H39NO19 | amino sugar | 1 | 1 |
| 673.2309:0.716:n | Sialyl-*N*-acetyllactosamine [b] | C25H42N2O19 | amino sugar | 1 | 1 |
| 230.0127:0.932:n | Paracetamol sulfate [b] | C8H9NO5S | sulfar conjugate | 1 | 1 |
| 353.1597:0.764:n | Propofol glucuronide [b] | C18H26O7 | drug metabolite | 2 | 1 |
| 369.1545:0.757:n | Hydroxypropofol glucuronide [b] | C18H26O8 | drug metabolite | 2 | 1 |
| 108.0456:1.041:n | *Unknown* [b] | C6H7NO | NA | 4 | 0 |
| 175.0612:0.881:n | 2-Isopropylmalic acid [b] | C7H12O5 | organic acid | 3 | 0 |
| 273.0802:0.789:n | *Unknown* [b] | C8H14N6O3S | NA | 4 | 0 |
| 375.2898:0.763:n | Lithocholic acid [b] | C24H40O3 | steroid | 2 | 0 |
| 593.3345:0.722:n | Stercobilin [b] | C33H46N4O6 | steroid | 3 | 0 |
| 598.3032:0.716:n | Urobilinogen [b] | C33H42N4O6 | steroid | 3 | 0 |
| 154.0499:0.865:n | Mesalamine [b] | C7H7NO3 | aminobenzoic acid | 2 | 1 |
| 160.0975:0.714:p | Acetylvaline [b] | C7H13NO3 | amino acid | 3 | 0 |
| 228.0979:0.844:p | Deoxycytidine [b] | C9H13N3O4 | purine | 3 | 0 |
| 291.1305:0.812:p | Arginosuccinate [b] | C10H18N4O6 | amino acid | 3 | 1 |
| 407.2385:1.015:p | *Unknown* [b] | C21H32N3O5 | NA | 4 | 0 |
| 471.2185:0.839:p | *Unknown* [b] | C20H26N10O4 | NA | 4 | 0 |

[a] *Compound that were removed with 75% missing rate cut-off but are added with 50 % cut-off value.*
[b] *Detection rate was lower than 50% for these metabolites.*

FIG. 8

Summary of 131 urinary metabolites detected in urine samples of pediatric IBD patients with *m/z*, RMT, ionization mode (p = ESI positive ion mode, n = ESI negative ion mode), molecular formula, chemical ID or tentative ID, confidence level of the ID and chemical classification based on HMDB. Column "common" indicates the common metabolites found in both urine and stool metabolite (1 = commonly found, 0 = not found in urine).

| *m.z*:RMT:mode | Chemical ID | Molecular Formula | Metabolite Class | Confirmed level | Common |
|---|---|---|---|---|---|
| 87.0452:1.607:n | Butyric acid | C4H8O2 | organic acid | 1 | 1 |
| 89.0244:1.131:n | Lactic acid | C3H6O3 | organic acid | 1 | 1 |
| 117.0193:1.826:n | Succinic acid | C4H6O4 | organic acid | 1 | 1 |
| 128.0353:1.102:n | Oxo-proline | C5H7NO3 | amino acid | 1 | 0 |
| 131.035:1.609:n | Glutaric acid | C5H8O4 | organic acid | 2 | 0 |
| 132.0302:1.025:n | Aspartic acid | C4H7NO4 | amino acid | 1 | 0 |
| 135.0299:0.995:n | Threonic acid | C4H8O5 | organic acid | 1 | 0 |
| 145.0506:1.473:n | 2-Methylglutaric acid | C6H10O4 | organic acid | 2 | 1 |
| 156.0657:0.917:n | Tiglylglycine | C7H11NO3 | organonitrogen | 3 | 0 |
| 157.051:1.429:n | Isopropylmaleate | C7H10O4 | organic acid | 2 | 0 |
| 159.1027:0.861:n | 7-Hydroxyoctanoic acid | C8H16O3 | organic acid | 3 | 0 |
| 160.0615:0.911:n | Aminoadipic acid | C6H11NO4 | amino acid | 1 | 0 |
| 166.0146:1.014:n | Quinolinic acid | C7H5NO4 | organic acid | 3 | 0 |
| 167.0201:0.968:n | Uric acid | C5H4N4O3 | organic acid | 1 | 1 |
| 172.9912:1.135:n | Phenyl sulfate | C6H6O4S | phenylsulfate | 2 | 0 |
| 178.051:0.914:n | Hippuric acid | C9H9NO3 | organic acid | 1 | 1 |
| 181.0506:0.903:n | 3-(3-Hydroxyphenyl)-3-hydroxypropanoic acid (HPHPA) | C9H10O4 | organic acid | 3 | 0 |
| 182.0459:0.948:n | 4-Pyridoxic acid | C8H9NO4 | organic acid | 1 | 1 |
| 184.0977:0.876:n | 2-Hepteneoylglycine | C9H15NO3 | amino acid | 3 | 0 |
| 187.0071:1.059:n | *p*-Cresol sulfate | C7H8O4S | phenylsulfate | 1 | 1 |
| 188.0353:0.926:n | Kynurenic acid | C10H7NO3 | Quinoline | 1 | 0 |
| 188.0558:1.35:n | acetylglutamate | C7H11NO5 | amino acid | 3 | 1 |
| 191.0552:0.895:n | Quinic acid | C7H12O6 | organic acid | 1 | 0 |
| 193.0357:0.882:n | Glucuronic acid | C6H10O7 | organic acid | 1 | 0 |
| 195.0524:0.888:n | dimethyluric acid/gluconate | C7H8N4O3 | purine | 3 | 0 |
| 197.0455:0.900:n | *Unknown* | C5H6N6O3 | NA | 4 | 0 |
| 201.1129:1.218:n | Sebacic acid | C10H18O4 | organic acid | 3 | 0 |
| 212.0023:1.025:n | Indoxyl sulfate | C8H7NO4S | phenylsulfate | 1 | 0 |
| 218.1034:0.836:n | Pantothenic acid | C9H17NO5 | organonitrogen | 1 | 1 |
| 222.9916:0.973:n | *Unknown* | C9H4O7 | NA | 4 | 0 |
| 225.0629:0.860:n | 5-Acetylamino-6-formylamino-3-methyluracil | C8H10N4O4 | NA | 3 | 0 |
| 227.9968:0.979:n | 5-Hydroxy-6-indolyl-O-sulfate | C8H7NO5S | phenylsulfate | 2 | 0 |
| 241.1193:0.824:n | *Unknown* | C7H14N8O2 | NA | 4 | 0 |

FIG. 8 continued

| | | | | | |
|---|---|---|---|---|---|
| 243.0771:0.845:n | Indolylacryloylglycine | C13H12N2O3 | amino acid | 3 | 0 |
| 269.15:0.805:n | Unknown | C8H22N4O6 | NA | 4 | 0 |
| 283.0823:0.809:n | p-Cresol-glucuronide | C13H16O7 | phenolic glycoside | 3 | 0 |
| 287.0227:0.912:n | 5'-(3',4'-Dihydroxyphenyl)-gamma-valerolactone sulfate | C11H12O7S | phenylsulfate | 3 | 0 |
| 290.0882:0.796:n | 2,3-Dehydro-2-deoxy-N-acetylneuraminic acid | C11H17NO8 | amino sugar | 1 | 0 |
| 302.114:0.812:n | Indoleacetyl glutamine | C15H17N3O4 | amino acid | 2 | 0 |
| 308.0987:0.791:n | N-Acetylneuraminic acid | C11H19NO9 | amino sugar | 1 | 1 |
| 331.1757:0.777:n | Neomenthol-glucuronide | C16H28O7 | O-glucuronide | 4 | 0 |
| 336.0725:0.794:n | Indole-3-carboxylic acid glucuronide | C15H15NO8 | O-glucuronide | 3 | 0 |
| 338.0881:0.791:n | 6-Hydroxy-5-methoxyindole glucuronide | C15H17NO8 | O-glucuronide | 3 | 0 |
| 345.1553:0.770:n | Unknown | C16H26O8 | NA | 3 | 0 |
| 347.0853:0.826:n | Unknown | C23H12N2O2 | NA | 4 | 0 |
| 350.088:0.788:n | Indole-3-acetic-acid-O-glucuronide | C16H17NO8 | O-glucuronide | 3 | 0 |
| 352.0868:0.863:n | 4-Hydroxybenzyl isothiocyanate 4"-acetylrhamnoside | C16H19NO6S | phenolic glycoside | 3 | 0 |
| 407.2803:0.750:n | Cholic acid | C24H40O5 | steroid | 1 | 1 |
| 464.3018:0.737:n | Glycocholic acid | C26H43NO6 | steroid | 1 | 1 |
| 481.2439:0.742:n | 11-beta-Hydroxyandrosterone-3-glucuronide | C25H38O9 | steroid | 3 | 0 |
| 525.2688:0.733:n | Unknown | C21H36N9O7 | NA | 4 | 0 |
| 539.2493:0.733:n | Tetrahydrocortisone-glucuronide | C27H40O11 | steroid | 3 | 0 |
| 541.2649:0.729:n | Cortolone-glucuronide | C27H42O11 | steroid | 2 | 0 |
| 543.2811:0.725:n | Cortol-3-glucuronide | C27H44O11 | steroid | 2 | 0 |
| 632.2044:0.717:n | Sialyllactose | C23H39NO19 | amino sugar | 1 | 1 |
| 673.2309:0.713:n | Sialyl-N-acetyllactosamine | C25H42N2O19 | amino sugar | 1 | 1 |
| 62.06:0.577:p | Ethanolamine | C2H7NO | amine | 1 | 0 |
| 76.0393:0.743:p | Glycine | C2H5NO2 | amino acid | 1 | 1 |
| 76.0757:0.594:p | Trimethylamine-N-oxide | C3H9NO | organonitrogen | 1 | 0 |
| 90.055:0.795:p | Alanine | C3H7NO2 | amino acid | 1 | 1 |
| 104.0706:0.94:p | Dimethylglycine | C4H9NO2 | amino acid | 1 | 0 |
| 104.0706:0.702:p | γ-Aminobutyric acid (GABA) | C4H9NO2 | amino acid | 1 | 1 |
| 104.1069:0.618:p | Choline | C5H14NO | organonitrogen | 1 | 1 |
| 106.0499:0.868:p | Serine | C3H7NO3 | amino acid | 1 | 1 |
| 114.0662:0.656:p | Creatinine | C4H7N3O | amino acid | 1 | 1 |
| 118.0611:0.737:p | Unknown | C3H7N3O2 | NA | 4 | 0 |
| 120.0652:0.905:p | Threonine | C4H9NO3 | amino acid | 1 | 1 |
| 129.0659:0.774:p | Dihydrothymine | C5H8N2O2 | purine | 3 | 0 |

FIG. 8 continued

| | | | | | |
|---|---|---|---|---|---|
| 131.1179:0.752:p | Acetylputriscine | C6H14N2O | amine | 1 | 1 |
| 132.0768:0.782:p | Creatine | C4H9N3O2 | amino acid | 1 | 1 |
| 133.0969:0.628:p | Ornithine | C5H12N2O2 | amino acid | 1 | 1 |
| 137.0457:1.039:p | Hypoxanthine | C5H4N4O | purine | 1 | 1 |
| 138.055:0.909:p | Trigonelline | C7H7NO2 | organic acid | 1 | 1 |
| 141.0659:0.734:p | imidazole propionate | C6H8N2O2 | organic acid | 2 | 1 |
| 146.0924:0.742:p | 4-Guanidinobutanoate | C5H11N3O2 | organic acid | 3 | 0 |
| 147.0764:0.926:p | Glutamine | C5H10N2O3 | amino acid | 1 | 1 |
| 147.1128:0.631:p | Lysine | C6H14N2O2 | amino acid | 1 | 1 |
| 150.0583:0.915:p | Methionine | C5H11NO2S | amino acid | 1 | 1 |
| 156.0767:0.667:p | Histidine | C6H9N3O2 | amino acid | 1 | 1 |
| 162.1125:0.757:p | Carnitine | C7H15NO3 | organonitrogen | 1 | 1 |
| 163.1077:0.654:p | 5-hydroxylysine | C6H14N2O3 | amino acid | 1 | 0 |
| 164.0748:0.769:p | Propyl-S-cysteine | C6H13NO2S | amino acid | 3 | 0 |
| 166.0723:0.744:p | Methylguanine | C6H7N5O | purine | 1 | 1 |
| 166.0863:0.94:p | Phenylalanine | C9H11NO2 | amino acid | 1 | 1 |
| 170.0924:0.681:p | 3-Methylhistidine | C7H11N3O2 | amino acid | 1 | 1 |
| 176.0658:0.876:p | Acetyl-aspartic acid | C6H9NO5 | amino acid | 3 | 1 |
| 182.0809:0.964:p | Tyrosine | C9H11NO3 | amino acid | 1 | 1 |
| 189.1598:0.651:p | Trimethyllysine | C9H20N2O2 | amino acid | 1 | 1 |
| 190.1191:0.954:p | Homocitrulline | C7H15N3O3 | amino acid | 1 | 0 |
| 191.0661:1.007:p | Aspartyl-glycine | C6H10N2O5 | amino acid | 3 | 1 |
| 195.0764:0.895:p | Aminohippuric acid | C9H10N2O3 | organic acid | 3 | 0 |
| 204.123:0.796:p | Acetyl-carnitine | C9H17NO4 | organonitrogen | 1 | 1 |
| 205.0972:0.938:p | Tryptophan | C11H12N2O2 | amino acid | 1 | 1 |
| 209.0921:0.887:p | Kynurenine | C10H12N2O3 | amino acid | 1 | 0 |
| 217.1294:0.869:p | Acetyl-arginine | C8H16N4O3 | amino acid | 3 | 0 |
| 222.0796:0.849:p | 5-(delta-carboxybutyl) Homocysteine | C8H15NO4S | amino acid | 2 | 0 |
| 223.0747:0.866:p | Cystathionine | C7H14N2O4S | amino acid | 1 | 0 |
| 232.1543:0.829:p | Butyryl carnitine | C11H21NO4 | organonitrogen | 2 | 0 |
| 238.0916:1.064:p | Xylosylserine | C8H15NO7 | amino sugar | 2 | 0 |
| 241.0311:0.946:p | Cystine | C6H12N2O4S2 | amino acid | 1 | 1 |
| 243.0981:0.91:p | Thymidine | C10H14N2O5 | pyrimidine | 2 | 0 |
| 244.1543:0.849:p | Tiglylcarnitine | C12H21NO4 | organonitrogen | 3 | 0 |
| 258.1084:0.862:p | Methylcytidine | C10H15N3O5 | pyrimidine | 3 | 0 |
| 259.0918:0.893:p | Ribothymidine | C10H14N2O6 | pyrimidine | 2 | 0 |
| 269.1238:0.926:p | Acetylcarnosine | C11H16N4O4 | amino acid | 1 | 0 |
| 276.1442:0.883:p | Glutaryl-carnitine | C12H21NO6 | organonitrogen | 3 | 0 |
| 282.1197:0.872:p | Methyl adenosine | C11H15N5O4 | purine | 1 | 0 |
| 286.2013:0.886:p | Fumaric acid, 2-dimethylaminoethyl heptyl ester | C18H25N2O | NA | 3 | 0 |
| 290.1598:0.897:p | Methylglutarylcarnitine | C13H23NO6 | organonitrogen | 3 | 0 |
| 291.1305:0.827:p | Arginosuccinate | C10H18N4O6 | amino acid | 3 | 1 |

FIG. 8 continued

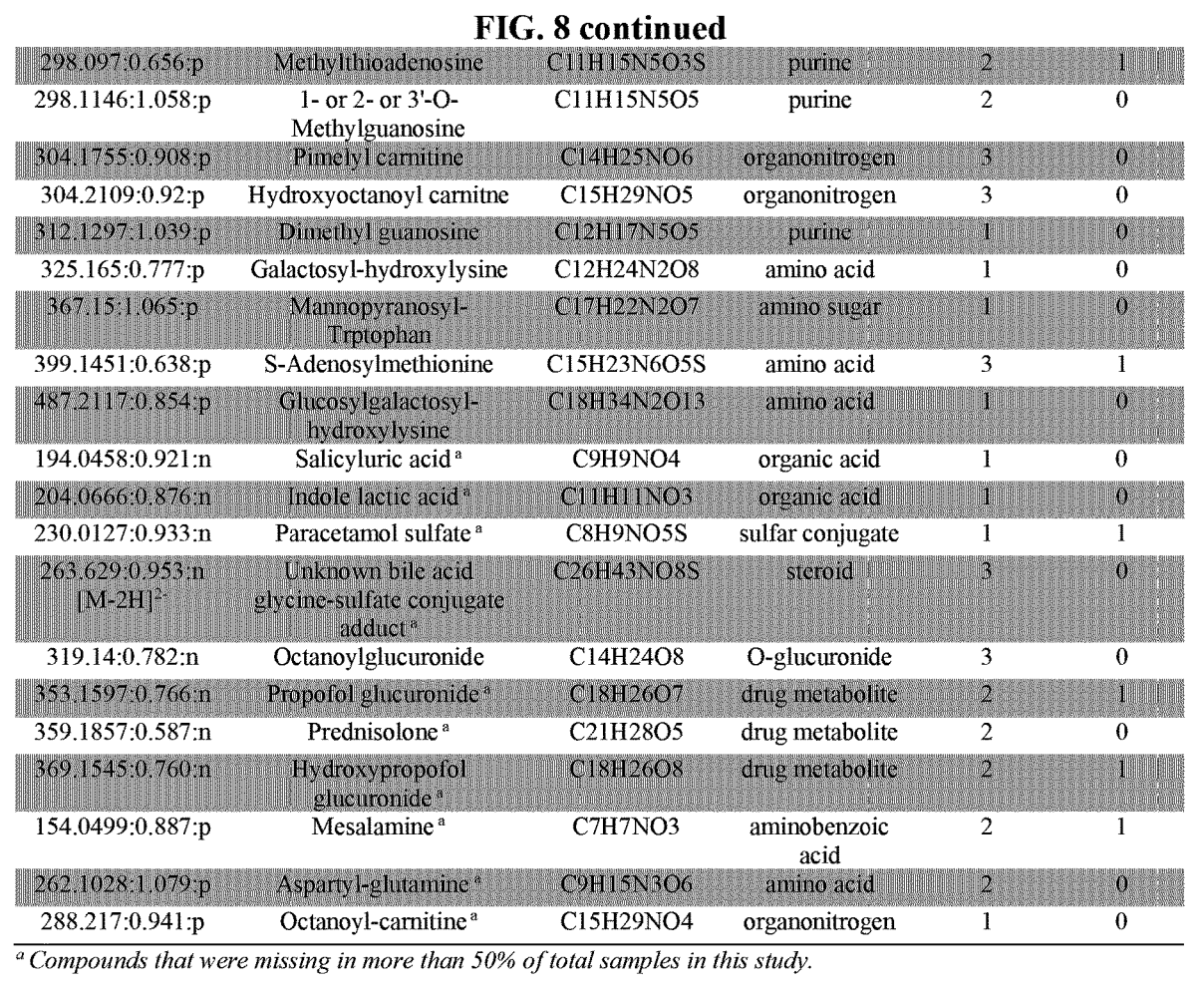

| | | | | | |
|---|---|---|---|---|---|
| 298.097:0.656:p | Methylthioadenosine | C11H15N5O3S | purine | 2 | 1 |
| 298.1146:1.058:p | 1- or 2- or 3'-O-Methylguanosine | C11H15N5O5 | purine | 2 | 0 |
| 304.1755:0.908:p | Pimelyl carnitine | C14H25NO6 | organonitrogen | 3 | 0 |
| 304.2109:0.92:p | Hydroxyoctanoyl carnitne | C15H29NO5 | organonitrogen | 3 | 0 |
| 312.1297:1.039:p | Dimethyl guanosine | C12H17N5O5 | purine | 1 | 0 |
| 325.165:0.777:p | Galactosyl-hydroxylysine | C12H24N2O8 | amino acid | 1 | 0 |
| 367.15:1.065:p | Mannopyranosyl-Trptophan | C17H22N2O7 | amino sugar | 1 | 0 |
| 399.1451:0.638:p | S-Adenosylmethionine | C15H23N6O5S | amino acid | 3 | 1 |
| 487.2117:0.854:p | Glucosylgalactosyl-hydroxylysine | C18H34N2O13 | amino acid | 1 | 0 |
| 194.0458:0.921:n | Salicyluric acid [a] | C9H9NO4 | organic acid | 1 | 0 |
| 204.0666:0.876:n | Indole lactic acid [a] | C11H11NO3 | organic acid | 1 | 0 |
| 230.0127:0.933:n | Paracetamol sulfate [a] | C8H9NO5S | sulfar conjugate | 1 | 1 |
| 263.629:0.953:n [M-2H]2- | Unknown bile acid glycine-sulfate conjugate adduct [a] | C26H43NO8S | steroid | 3 | 0 |
| 319.14:0.782:n | Octanoylglucuronide | C14H24O8 | O-glucuronide | 3 | 0 |
| 353.1597:0.766:n | Propofol glucuronide [a] | C18H26O7 | drug metabolite | 2 | 1 |
| 359.1857:0.587:n | Prednisolone [a] | C21H28O5 | drug metabolite | 2 | 0 |
| 369.1545:0.760:n | Hydroxypropofol glucuronide [a] | C18H26O8 | drug metabolite | 2 | 1 |
| 154.0499:0.887:p | Mesalamine [a] | C7H7NO3 | aminobenzoic acid | 2 | 1 |
| 262.1028:1.079:p | Aspartyl-glutamine [a] | C9H15N3O6 | amino acid | 2 | 0 |
| 288.217:0.941:p | Octanoyl-carnitine [a] | C15H29NO4 | organonitrogen | 1 | 0 |

[a] Compounds that were missing in more than 50% of total samples in this study.

METHOD OF DIAGNOSING AND TREATMENT MONITORING OF CROHN'S DISEASE AND ULCERATIVE COLITIS

FIELD OF THE INVENTION

The present invention generally relates to the field of inflammatory bowel disease (IBD), and in particular, relates to methods of differentiating Crohn's disease (CD) and ulcerative colitis (UC), as well as methods of monitoring treatment of CD and UC.

FIELD OF THE INVENTION

Inflammatory bowel disease (IBD), including Crohn's disease (CD) and ulcerative colitis (UC), is a idiopathic chronic gastrointestinal (GI) condition that carries a significant burden of disease in pediatric populations with about 20-30% of IBD patients experiencing their first symptoms before the age of 18 years. Children who develop IBD are uniquely affected by its unpredictable course and atypical symptoms, which impairs normal growth and development, including a higher risk for depression. The early onset of IBD also significantly impacts overall quality of life with long-term complications, including fibrosis, stricturing and the need for intestinal resections. As a result, early diagnosis and treatment is critical to manage inflammation while preserving normal GI function. While anatomic differences help differentiate CD from UC, there are no validated serological or stool biochemical markers (i.e., biomarkers) that can accurately distinguish between these two disease subtypes. Therefore, repeat endoscopic imaging and histopathological assessment of IBD activity and mucosal healing are necessary for reliable diagnosis despite their invasiveness. These procedures are also costly, may contribute to delays in diagnosis due to tissue biopsy handling and do not always lead to conclusive results notably for early onset IBD, such as indeterminate colitis highlighting the complex disease spectrum in affected children. These diagnostic dilemmas reflect the poorly understood etiology of pediatric IBD which often exhibit more aggressive or complicated disease courses than adults that is mediated by a complex interplay of genetic, immunological and environmental factors.

Metabolomics offers a systemic approach for characterizing the molecular phenotype of an organism since metabolites represent real-world end-products of gene expression and protein activity, as well as bioactive molecules reflecting habitual diet and lifelong exposures. To date, metabolomics studies have been largely focused on understanding the pathophysiology of IBD by comparing metabolic differences between IBD patients and healthy controls when analyzing serum/plasma, urine or stool specimens. Previous studies have reported significant changes in microbial derived metabolites reflecting underlying dysbiosis of commensal gut microbiota communities, such as secondary bile acids, butyric acid, and/or trimethylamine in fecal water extracts when using nuclear magnetic resonance (NMR) and liquid-chromatography-mass spectrometry (LC-MS). Given the clinical manifestations of IBD, such as fatigue and weight loss with poor nutrient absorption, several studies have reported down-regulated amino acid metabolism and organic acids from the citric acid cycle that reflects impairments in energy homeostasis. In contrast to clear differences between healthy controls and patients with IBD, differentiation between CD and UC based on metabolic profiles have proven far more elusive often with contradictory results. Several studies reported significantly lower levels of human-microbial co-metabolites, including p-cresol sulfate and hippuric acid in urine samples from CD patients as compared to UC and healthy controls. In contrast, no significant differences were reported in an independent cohort of CD and UC patients when using the same sample workup protocol and analytical platform for metabolomics. Similarly in stool samples, reduced levels of short-chain fatty acids (e.g., butyric acid, propionic acid) have been reported in adult CD as compared to UC patients and healthy controls; however these same stool derived metabolites failed to differentiate CD from UC in a recent study that focused on pediatric IBD patients.

Adult IBD patients often require intestinal resections for treatment or management of their disease that is further confounded by long-term pharmacological interventions that likely alter the composition of the gut microbiome. On the other hand, pediatric populations are typically recently diagnosed patients who are often treatment naïve, which may explain conflicting reports between a handful of pediatric cases and the majority of metabolomic studies involving heterogeneous adult IBD patients. Additionally, the importance of sample quality and metabolite stability involving the collection, storage and workup of stool specimens with high biological activity has rarely been investigated, which is a major source of false discoveries. Lastly, integration of microbiome profiles, especially the investigation of their functional potential, is still in its infancy despite the complex interplay of host-microbial co-metabolism.

It would be desirable, thus, to characterize the metabolic phenotype of pediatric IBD patients to permit diagnosis early in disease progression, e.g. before the onset of medications or surgeries, as a way to reduce potential confounding and false discoveries.

SUMMARY OF THE INVENTION

Distinct metabolic phenotypes of IBD patients have now been determined, thereby permitting differentiation between Crohn's disease (CD) and ulcerative colitis (UC), allowing for early diagnosis and to facilitate treatment monitoring while also potentially avoiding the need for invasive colonoscopic imaging and tissue biopsies.

In one aspect of the invention, a method of differentiating between UC and CD in a subject is provided comprising:

i) detecting in a urine sample from the subject the level of at least two metabolic biomarkers selected from the group consisting of serine, hypoxanthine, kynurenine, threonine, indoxylsulfate, phenylacetylglutamine, 5-hydroxy-6-indolyl-O-sulfate, 5-($\delta$-carboxybutyl) homocysteine, sialic acid and an anion having m/z: RMT:polarity of 345.1553:0.770:n;

ii) comparing the level of the detected biomarkers to a standard, UC or CD control level and determining the difference between the biomarker level and the selected control level;

iii) a) determining that the subject has UC when the level of serine, hypoxanthine, kynurenine, and threonine exhibit is statistically greater than the standard or CD control level or the level of indoxylsulfate, phenylacetylglutamine, 5-hydroxy-6-indolyl-O-sulfate, 5-($\delta$-carboxybutyl) homocysteine, sialic acid and an anion having m/z:RMT:polarity of 345.1553:0.770:n is statistically less than the standard or CD control level, or b) determining that the subject has CD when the levels of indoxylsulfate, phenylacetylglutamine, 5-hydroxy-6-indolyl-O-sulfate, 5-($\delta$-carboxybutyl)

homocysteine, sialic acid, and an anion having m/z: RMT:polarity of 345.1553:0.770:n is statistically greater than the UC control level, or the level of serine, hypoxanthine, kynurenine, and threonine is statistically less than the standard UC control level; and iv) optionally, treating the subject with one or more of an anti-inflammatory, corticosteroid, antibiotic, biologic, immunomodulatory, modified diet and surgery.

In another aspect of the invention, a method of differentiating between UC and CD in a subject is provided comprising:

i) detecting in a stool (fecal) specimen from the subject the level of at least two metabolite biomarkers selected from the group consisting of ketodeoxycholic acid, cholic acid, choline, tryptophan, trimethyllysine, serine, butyric acid, lactic acid, hypoxanthine and guanine;

ii) comparing the level of the detected biomarkers to a standard, UC or CD control level and determining the difference between the biomarker level and the selected control level;

iii) a) determining that the subject has UC when the stool level of serine, tryptophan, choline, hypoxanthine and lactic acid is statistically greater than the standard or CD control level or the level of ketodeoxycholic acid, cholic acid, butyric acid, trimethyllysine, and guanine is statistically less than the standard or CD control level, or b) determining that the subject has CD when the stool level of serine, tryptophan, choline, hypoxanthine and lactic acid is statistically less than the standard or UC control level or the level of ketodeoxycholic acid, cholic acid, butyric acid, trimethyllysine, and guanine is statistically more than the standard or UC control level; and iv) optionally, treating the subject with one or more of an anti-inflammatory, corticosteroid, antibiotic, biologic, immunomodulatory, modified diet and surgery.

In a further aspect of the invention, a method of monitoring in a subject with UC or CD adherence to prescribed exclusive enteral nutrition (EEN) therapy comprising:

i) obtaining a urine sample from the subject at a period of time following the initiation of prescribed EEN therapy;

ii) detecting in the urine sample the level of at least one of octanoylcarnitine, pantothenic acid and pyridoxic acid; and iii) determining that the subject has adhered and/or is responsive to the EEN therapy when the level of octanoylcarnitine, pantothenic acid and/or pyridoxic acid is increased in comparison to a control or baseline level.

These and other aspects of the invention are described herein by reference to the following figures.

BRIEF DESCRIPTION OF THE FIGURES

FIG. 5. Top-ranked ratiometric biomarkers identified by MSI-CE-MS that differentiate CD from UC in osmolality normalized urine.

FIG. 7. Summary of 104 stool metabolites measured in samples of pediatric IBD patients with m/z, RMT, ionization mode (p=ESI positive ion mode, n=ESI negative ion mode), molecular formula, chemical ID or tentative ID, confidence level of the ID and chemical classification based on Human Metabolome Database (HMDB). Column "common" indicates the common metabolites found in both urine and stool metabolite (1=commonly found, 0=not found in urine).

FIG. 8. Summary of 131 urinary metabolites detected in urine samples of pediatric IBD patients with m/z, RMT, ionization mode (p=ESI positive ion mode, n=ESI negative ion mode), molecular formula, chemical ID or tentative ID, confidence level of the ID and chemical classification based on HMDB. Column "common" indicates the common metabolites found in both urine and stool metabolite (1=commonly found, 0=not found in urine).

Figure 1:
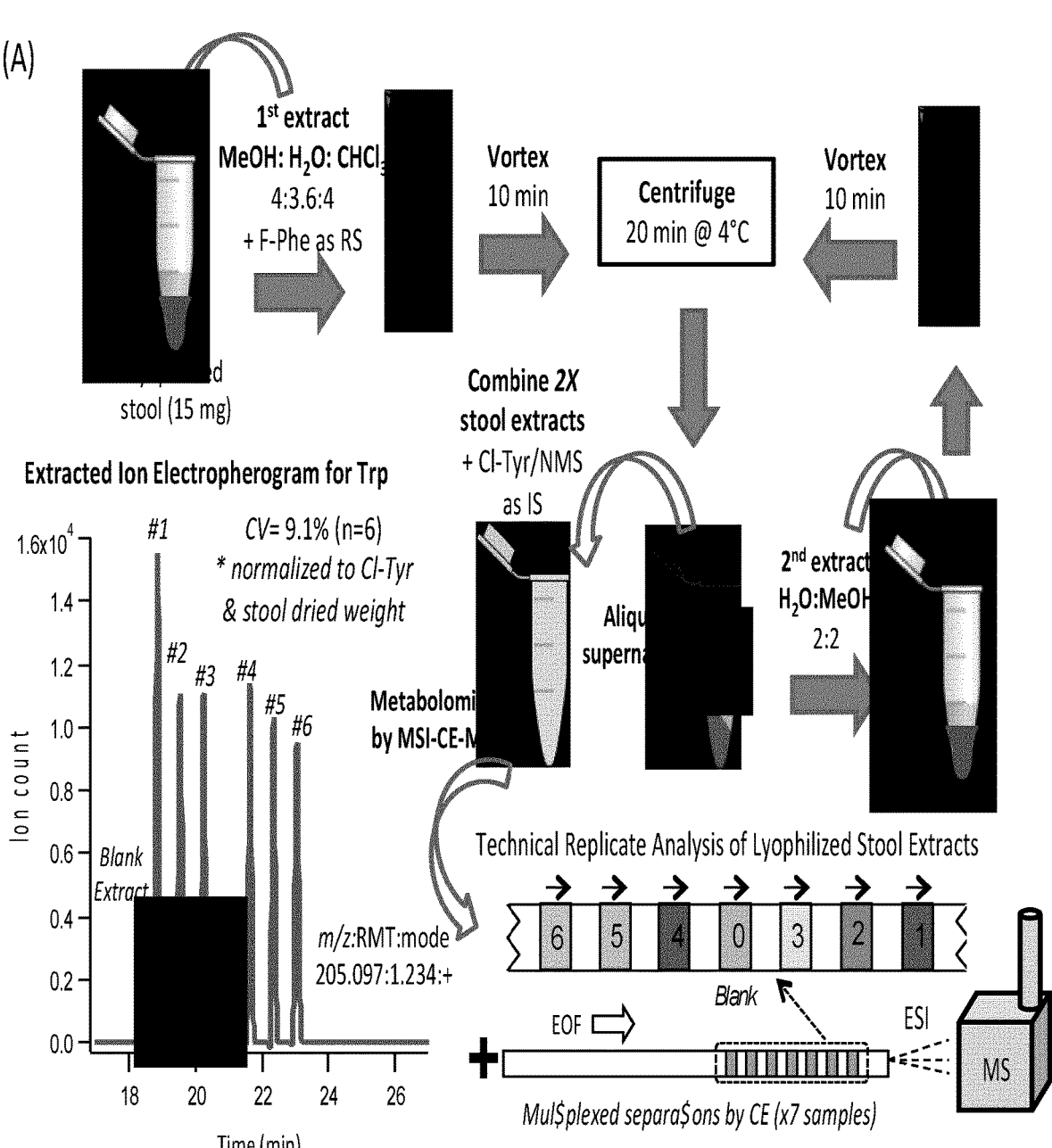
FIG. 1. (A) Stool extraction protocol and high throughput metabolite screening platform in MSI-CE-MS to identify reproducible yet representative molecular features and authenticate metabolites of clinical significance (B) Metabolomics data workflow for metabolite authentication from stool extracts with stringent quality control. (C) Control chart for recovery standard (F-Phe) included in every stool extract to monitor long-term technical precision when conducting metabolomic studies by MSI-CE-MS under positive and negative ion mode detection with few outliers outside warning limits (±2 s). In contrast, urine samples were analyzed directly by MSI-CE-MS after dilution with deionized water.

5 of both urinary metabolites following the initiation of EEN as compared to CS therapy at 2 and 4 weeks relative to baseline levels when using a repeat measures 2-way ANOVA with strong effect sizes. Also, metabolic trajectories for urinary octanoylglucuronide and pyridoxic acid are also shown for individual IBD patients in the two treatment arms (CD-EEN; UC/CD-CS, n=8) over the full 8 week intervention, including one CD patient who was later switched to EEN from CS after 2-3 weeks (CD-CS/EEN). This clinical treatment course change is more evident in the urinary excretion of octanoylglucuronide than pantothenic acid.

DETAILED DESCRIPTION OF THE INVENTION

The present invention relates to methods of differentiating between UC and CD in a subject.

In one aspect of the invention, the method comprises detecting in a urine sample from the subject the level of at least two metabolic biomarkers selected from the group consisting of serine, hypoxanthine, kynurenine, threonine, indoxylsulfate, phenylacetylglutamine, 5-hydroxy-6-indolyl-O-sulfate, 5-(δ-carboxybutyl) homocysteine, sialic acid and an anion having m/z:RMT:polarity of 345.1553:0.770:n; comparing the level of the detected biomarkers to a standard, UC or CD control level and determining the difference between the biomarker level and the selected control level; a) determining that the subject has UC when the level of serine, hypoxanthine, kynurenine, and threonine exhibit is statistically greater than the standard or CD control level or the level of indoxylsulfate, phenylacetylglutamine, 5-hydroxy-6-indolyl-O-sulfate, 5-(δ-carboxybutyl) homocysteine, sialic acid and an anion having m/z:RMT:polarity of 345.1553:0.770:n is statistically less than the standard or CD control level, or b) determining that the subject has CD when the levels of indoxylsulfate, phenylacetylglutamine, 5-hydroxy-6-indolyl-O-sulfate, 5-(δ-carboxybutyl) homocysteine, sialic acid, and an anion having m/z:RMT:polarity of 345.1553:0.770:n is statistically greater than the UC control level, or the level of serine, hypoxanthine, kynurenine, and threonine is statistically less than the standard UC control level.

In another aspect of the invention, the method comprises: detecting in a stool (fecal) specimen from the subject the level of at least two metabolite biomarkers selected from the group consisting of ketodeoxycholic acid, cholic acid, choline, tryptophan, trimethyllysine, serine, butyric acid, lactic acid, hypoxanthine and guanine; comparing the level of the detected biomarkers to a standard, UC or CD control level and determining the difference between the biomarker level and the selected control level; a) determining that the subject has UC when the stool level of serine, tryptophan, choline, hypoxanthine and lactic acid is statistically greater than the standard or CD control level or the level of ketodeoxycholic acid, cholic acid, butyric acid, trimethyllysine, and guanine is statistically less than the standard or CD control level, or b) determining that the subject has CD when the stool level of serine, tryptophan, choline, hypoxanthine and lactic acid is statistically less than the standard or UC control level or the level of ketodeoxycholic acid, cholic acid, butyric acid, trimethyllysine, and guanine is statistically more than the standard or UC control level.

As used herein, ulcerative colitis refers to a condition in which the innermost lining of the colon, the mucosa, becomes inflamed. Ulcerative colitis spreads proximally from the rectum and can spread continuously to the rest of the large intestine (colon).

Crohn's disease, on the other hand, refers to an inflammatory condition that may affect any part of the gastrointestinal (GI) tract, from the lips to the anus. The areas most often affected, however, are the lower part of the small intestine (ileum) and the large intestine (colon). Unlike ulcerative colitis, inflammation in Crohn's can skip large segments of bowel before reappearing in other segments, and may burrow beyond the mucosa through the entire thickness of the bowel wall.

The term "subject" refers to a mammalian subject, preferably a human subject, including both adults and pediatric subjects, i.e. patients under the age of 18 years.

To conduct the method, a urine or fecal stool sample is obtained from the subject in the usual manner. The urine sample may be a single-spot/random urine sample. The fecal or stool sample is collected, free from water and urine, combined with suitable solvents and freeze-dried. Samples were then extracted (stool) or diluted (urine) in aqueous solution for testing.

Once the sample is obtained, it is analyzed to determine the signal response or concentration of the selected biomarker(s) in the sample. As one of skill in the art will appreciate, biomarker level may be determined using one of several techniques established in the art that would be suitable for detecting such biomarkers, e.g. metabolites, in the urine sample, including mass spectrometry, capillary electrophoresis, chromatographic techniques such as high performance liquid chromatography and gas chromatography, immunoassay or enzyme-based assays with colorimetric, fluorescence or radiometric detection. As one of skill in the art will appreciate, the present biomarkers may be analyzed directly or may be chemically derivatized for analysis, and may be analyzed by comparison against stable-isotope internal standards.

In one embodiment, biomarker detection using a mass spectrometry (MS)-based method is used. Suitable MS-based methods for use include direct infusion-mass spectrometry, electrospray ionization (ESI)-MS, desorption electrospray ionization (DESI)-MS, direct analysis in real-time (DART)-MS, atmospheric pressure chemical ionization (APCI)-MS, electron impact (EI) or chemical ionization (CI), as well as MS-based methods coupled with a separation technique, such as liquid chromatography (LC-MS), gas chromatography (GC-MS), or capillary electrophoresis (CE-MS) mass spectrometry.

In other embodiments, the level of a biomarker in a sample may be measured by immunoassay using an antibody specific to the target biomarker. The antibody binds to the biomarker and bound antibody is quantified by measuring a detectable marker which may be linked to the antibody or other component of the assay, or which may be generated during the assay. Detectable markers may include radioactive, fluorescent, phosphorescent and luminescent (e.g. chemiluminescent or bioluminescent) compounds, dyes, particles such as colloidal gold and enzyme labels. The term "antibody" is used herein to refer to monoclonal or polyclonal antibodies, or antigen-binding fragments thereof, e.g. an antibody fragment that retains specific binding affinity for the target biomarker. Antibodies to the target biomarkers may be commercially available. Alternatively, antibodies to the target biomarkers may also be raised using techniques conventional in the art. For example, antibodies may be made by injecting a host animal, e.g. a mouse or rabbit, with the antigen (target biomarker), and then isolating antibody from a biological sample taken from the host animal. Alternative affinity ligands that bind to CF-specific metabolites may also be utilized for measurement of CF metabolites, such as DNA or RNA-based aptamers derived from systematic evolution of ligands by exponential enrichment (SELEX).

Different types of immunoassay may be used to determine the level of target biomarkers in a urine sample, including indirect immunoassay in which the biomarker is non-specifically immobilized on a surface; sandwich immunoassay in which the biomarker is specifically immobilized on a surface by linkage to a capture antibody bound to the surface; and a competitive binding immunoassay in which a sample is first combined with a known quantity of biomarker antibody to bind biomarker in the sample, and then the sample is exposed to immobilized biomarker which competes with the sample to bind any unbound antibody. Enzyme Linked ImmunoSorbent Assay (ELISA) may also be used to determine the level of a biomarker in a sample. In this case, the biomarker to be analyzed is generally immobilized on a solid support, complexed with an antibody to the biomarker which is itself linked to an enzyme indicator, such as horseradish peroxidase (HRP), alkaline phosphatase (AP), $\beta$-galactosidase, acetylcholinesterase and catalase. Detection may then be accomplished by incubating this enzyme-complex with a substrate for the enzyme that yields a detectable product.

The method includes the measurement of the level of at least two metabolites as specific biomarkers for CD or UC from the urine or stool sample. Preferably, the level of at least two to five or more biomarkers is determined to diagnose CD or UC, i.e. a panel of biomarkers is utilized.

Once the level of the selected biomarker(s) is determined, the level is compared to a control level to determine the average fold-change (FC) difference and statistical significance (p-value) between the biomarker measured in urine sample relative to a standard control group (e.g., the level of the biomarker in healthy subjects), a CD control (e.g. the level of the biomarker in CD subjects), or a UC control (e.g. the level of the biomarker in UC subjects). Preferably control levels are mean levels from matched subjects (e.g. age-, gender- and/or ethnically-matched to a population).

A subject is determined to have UC when the urine level of serine, hypoxanthine, kynurenine, and threonine exhibit is statistically greater than the standard or CD control level (i.e. exhibits a fold-change >1), or when the urine level of indoxylsulfate, phenylacetylglutamine, 5-hydroxy-6-indolyl-O-sulfate, 5-($\delta$-carboxybutyl) homocysteine, sialic acid and/or an anion having m/z:RMT:polarity of 345.1553:0.770:n is statistically less than the standard or CD control level (i.e. exhibits a fold-change >1). Alternatively, the subject is determined to have UC when the stool level of serine, tryptophan, choline, hypoxanthine and/or lactic acid is statistically greater than the standard or CD control level, or the stool level of ketodeoxycholic acid, cholic acid, butyric acid, trimethyllysine, and/or guanine is statistically less than the standard or CD control level.

A subject is determined to have CD when the urine level of indoxylsulfate, phenylacetylglutamine, 5-hydroxy-6-indolyl-O-sulfate, 5-($\delta$-carboxybutyl) homocysteine, sialic acid or an anion having m/z:RMT:polarity of 345.1553:0.770:n is statistically greater than the standard or UC control level, or the urine level of serine, hypoxanthine, kynurenine, or threonine is statistically less than the standard or UC control level. Alternatively, the subject has CD when the stool level of serine, tryptophan, choline, hypoxanthine and/or lactic acid is statistically less than the standard or UC control level, or the stool level of ketodeoxycholic acid, cholic acid, butyric acid, trimethyllysine, and/or guanine is statistically more than the standard or UC control level.

The present method of differentiating between UC and CD may additionally include the detection of one or more biomarker levels in stool samples from a subject. The biomarkers include one or more of tryptophan, lactic acid, threonine, choline, serine, ketodeoxycholic acid, cholic acid, hypoxanthine, trimethyllysine, butyric acid and guanine. When the level of one or more of tryptophan, lactic acid, hypoxanthine, choline, or serine is statistically significantly greater than the standard or CD control level, or the level of one or more of ketodeoxycholic acid, cholic acid, trimethyllysine, butyric acid or guanine is statistically significantly less than the standard or CD control level, this confirms a diagnosis of UC. On the other hand, when the level of one or more of ketodeoxycholic acid, cholic acid, trimethyllysine, butyric acid or guanine is statistically significantly greater than the standard or UC control level, or tryptophan, lactic acid, threonine, choline, serine or hypoxanthine is statistically significantly less than the standard or CD control level, this confirms a diagnosis of CD.

In addition to the quantitation of selected biomarkers, a ratiometric determination of two biomarkers may be calculated, i.e. the ratio of the levels of two biomarkers from a sample, that may be compared against a control value, i.e. the ratio of the control levels of the two selected biomarkers. Preferred ratiometric determinations for use in the present method are between a metabolite biomarker that exhibits an increased level in one of CD or UC, and a metabolite biomarker that exhibits a reduced level in the same disease (CD or UC). Such a ratio further amplifies the fold-change of the selected biomarkers and increases statistical significance (p value) for CD or UC diagnosis, while also correcting for differences in sample volume in a specimen analyzed. Thus, ratios of higher expressed urine metabolites in CD such as indoxylsulfate, phenylacetylglutamine, phenyl sulfate and 5-hydroxy-6-indolyl-o-sulfate, to lower expressed metabolites such as serine, hypoxanthine, kynurenine, and threonine may be determined for use in the present methods. Examples of ratios determined to exhibit high specificity for differentiating between CD and UC include, but are not limited to, the ratio of the level of serine to indoxylsulfate in urine samples, and the ratio of the level of guanine to choline stool samples. Other examples are provided in FIG. 5.

A subject is determined to have CD or UC when the difference in the level of the detected biomarkers is statistically different (statistically increased or decreased) from a control level of these biomarkers, and/or when the difference in a ratiometric determination between two biomarkers is statistically different from the control ratio between these biomarkers above a minimum control threshold established for a population. The determination of statistical significance is well-established in the art. Statistical significance is attained when a p-value is less than the significance level. The p-value is the probability of observing an effect given that the null hypothesis is true whereas the significance or alpha (a) level is the probability of rejecting the null hypothesis given that it is true. Generally, a statistically significant difference, i.e. increase or decrease, in the level of a biomarker in accordance with the present method, is a difference in the level of the biomarker from the control level of at least about 5%, or greater, e.g. at least about 10%, 15%, 20%, 25% or more. When performing multivariate statistical analysis during biomarker discovery in metabolomics, corrected p-values are often used to correct for multiple hypothesis testing in order to reduce false discoveries, such as the use of a false discovery rate (q<0.05) or a more conservative Bonferroni correction.

As one of skill in the art will appreciate, the present methods may be adapted for the diagnosis of UC or CD separately.

Thus, for the diagnosis of UC, the method comprises detecting in a urine sample from the subject the level of at least two metabolic biomarkers selected from the group consisting of serine, hypoxanthine, kynurenine, and threonine; comparing the level of the detected biomarkers to a standard control level and determining the difference between the biomarker level and the selected control level; determining that the subject has UC when the level of selected biomarkers is statistically greater than the standard control level. The detection of the level of one or more of serine, tryptophan, choline, hypoxanthine, or lactic acid in a stool sample may additionally be determined, wherein a statistically significant increase in the level of one or more of these stool biomarkers than the standard control level is indicative of UC.

For the diagnosis of CD, the method comprises detecting in a urine sample from the subject the level of at least two metabolic biomarkers selected from the group consisting of sialic acid, indoxylsulfate, phenylacetylglutamine, 5-hydroxy-6-indolyl-O-sulfate, 5-(δ-carboxybutyl) homocysteine, or an anion having m/z:RMT:polarity of 345.1553: 0.770:n; comparing the level of the detected biomarkers to a standard control level and determining the difference between the biomarker level and the selected control level; determining that the subject has CD when the level of selected biomarkers is statistically greater than the standard control level. The detection of the level of one or more of ketodeoxycholic acid, cholic acid, trimethyllysine, butyric acid and guanine in a stool sample may additionally be determined, wherein a statistically significant increase in the level of one or more of these stool biomarkers than the standard control level is indicative of CD.

Following diagnosis of one or the other of Crohn's disease or ulcerative colitis, an appropriate treatment may then be selected.

For Crohn's disease, treatment may include administration of one or a combination of medications such as anti-inflammatory drugs, e.g. 5-aminosalicylic acid (5-ASA) for mild to moderate disease, or corticosteroids for more severe disease; antibiotics to treat bacteria found in the gut, which may be a contributing factor to the development of Crohn's disease and/or to treat infection associated with perianal disease, fistulae, and abscesses; immunomodulators may be used to induce or prolong remissions such as 6-mercaptopurine, azathioprine or methotrexate; and biologics such as infliximab (Remicade™), adalimumab (Humira™), vedolizumab (Entyvio™) and ustekinumab (Stelara™). A modified diet may be prescribed to avoid foods that are difficult to digest and could result in an obstruction in a narrowed segment of bowel, including foods such as popcorn, uncooked vegetables, nuts, milk, and certain spices or spicy foods. In some cases, exclusive enteral nutrition (EEN) (administered through a nasogastric tube). In some cases, surgery may be necessary when medication and diet have failed, or when other issues arise. Thus, surgery may involve removal of diseased bowel, to treat severe narrowing or obstruction of the intestines, intractable hemorrhaging, intestinal fistulae or perforation, or to drain an abscess.

Treatment for ulcerative colitis may also include medications such as anti-inflammatory drugs, antibiotics and immunomodulators, as well as modified diet. Generally, ulcerative colitis exhibits less severe symptoms to those of Crohn's disease, and thus, the treatment regimen is often less aggressive, for example, and may not include steroid treatment. Exclusive enteral nutrition (EEN) has not been validated for UC, and thus, is less likely to be utilized in UC treatment. Surgical treatment would also differ given that UC and CD each target different parts/regions of the bowel.

In addition to use to diagnose and differentiate between UC and CD, the present methods may also be used to predict disease progression and/or monitor treatment response to therapy. Generally, by monitoring the levels of selected biomarkers over time or throughout the course of a treatment, changes in biomarker levels may be indicative of disease progression or regression, which may be as a result of treatment. In this regard, biomarkers that are elevated in the disease state may remain elevated or exhibit increased elevation on progression of disease and/or lack of response to treatment, or may exhibit a decreased or decreasing level which is evidence disease regression and/or response to treatment. Alternatively, biomarkers that exhibit reduced levels in the disease state may remain at these levels or exhibit further level reduction on progression of disease and/or lack of response to treatment, or may exhibit increased or increasing levels which evidence disease regression and/or response to treatment.

In another aspect, a method of monitoring adherence or treatment response to prescribed exclusive enteral nutrition (EEN) therapy in a subject with UC or CD is also provided. The method comprises obtaining a urine sample from the subject at a period of time following the initiation of prescribed EEN therapy, e.g. within about 1-8 weeks of the onset of the EEN treatment, preferably within about 2, 3, 4, 5, 6, 7 or 8 weeks. Using methods as outlined herein, the level of at least one of octanoylcarnitine, pantothenic acid and pyridoxic acid is detected in the sample. Adherence to EEN therapy is confirmed when the level of octanoylcarnitine, pantothenic acid and/or pyridoxic acid is increased in comparison to a control or baseline level of these biomarkers, e.g. the level of these biomarkers in a urine sample from the subject prior to EEN therapy, or the level of these biomarkers in an untreated control. Increased levels of the biomarkers of at least 1-fold and preferably greater, e.g. 2, 5, 8, 10 or greater fold increase, is indicative of adherence to or treatment response to EEN therapy in which clinical remission or inflammation reduction is induced in treated patients.

The present methods, based on metabolite phenotyping, advantageously provide a means to diagnose IBD patients early in their disease progression, in a non-invasive manner, to avoid endoscopic imaging and histopathological assessment of IBD activity and mucosal healing. The present methods are also more efficient than conventionally used invasive procedures, which are more costly, may contribute to delays in diagnosis due to tissue biopsy handling and do not always lead to conclusive results.

The present methods may be conducted using a kit useful to detect target biomarkers. Such a kit comprises biomarker-specific reactants, i.e. a reactant that specifically reacts or binds with each target biomarker as selected from those described in the foregoing description. The reactants may be provided bound to a solid support, for example, as a panel, allowing a urine sample or an extracted stool sample to simply be spotted onto the support to determine the presence or absence of each biomarker in the sample. The reaction between the reactant and its biomarker is detectable, either by the release of a detectable marker (such as a colorimetric or other marker), or by subsequent labelling of the biomarker to detect binding to its reactant, as would be appreciated by one of skill in the art.

Embodiments of the invention are described by reference to the following specific example which is not to be construed as limiting.

Example 1

Various methods were employed to determine distinct biomarkers associated with Crohn's disease and distinct biomarkers associated with ulcerative colitis, i.e. biomarkers not common to both.

Methods

Chemicals and reagents. All chemicals were purchased from Sigma Aldrich (St. Louis, MO, USA) unless otherwise stated. For preparation of buffer and sheath liquid, ultra-grade LC-MS solvents (water, methanol and acetonitrile) obtained from Caledon Laboratories Ltd. (Georgetown, ON, Canada) were used. Stock solutions for calibrants, sheath liquid and buffer solutions were all prepared in deionized water (Barnstead EASY-pure II LF ultrapure water system (Dubuque, IA, USA).

Pediatric IBD study cohort. This study was approved by the Hamilton Integrated Research Ethics Board (#15-365) and parental consent was obtained for all the participants. The study enrolled children from 5 to 18 years old who had been diagnosed with IBD by endoscopy, histology and radiography at McMaster Children's Hospital. Patients were included if they were admitted to hospital to be initiated on exclusive enteral nutrition therapy, or intravenous corticosteroids for induction of remission of CD or UC. Patients were excluded if they were younger than 5 years, received antibiotic therapy, or did not require admission to hospital. None of these patients have undergone resection surgery.

Urine and fecal sample collection, storage and workup procedure. All urine and stool samples included in this study were collected prior to induction therapy (i.e. corticosteroid or exclusive enteral nutrition) at McMaster Children's Hospital. Single-spot urine samples were collected in the morning and did not necessarily represent the first morning urine void. Following collection, 1 mM of sodium azide was added to all urine samples as an antimicrobial preservative and then samples were stored in a fridge before being transferred to a freezer at −80° C. All thawed urine samples (on ice) were prepared by a simple dilution (from 5 to 10-fold) using 25 µL of urine in ultra-grade LC-MS water containing the internal standards, 3-chloro-L-tyrosine (Cl-Tyr) and sodium 2-naphthalenesulfonate (NMS) to the final internal standards concentration of 10 µM each, which was followed by mixing using a vortex for 30 s. Also, stool specimens were aliquoted into two tubes at the clinic, one for metabolomics analysis and the other for microbiome analysis, into 1.5 mL centrifuge tubes and then placed in a freezer at −80° C. at the earliest time possible. For metabolomics analysis, frozen stool samples were transferred to 15 mL Falcon tubes and lyophilized (Labconco FreeZone Freeze Dry System; MO, USA) over approximately two days. Freeze-dried stool samples were then weighed out (15-20 mg) accurately prior to performing a modified Bligh Dyer extraction. After ensuring that all samples are completely dry, each sample was mixed with pre-chilled methanol, deionized water and chloroform at 4:3.6:4 ratio with a total volume of 424 µL. Methanol was added to increase solubility of polar but relatively hydrophobic metabolites such as bile acids, and to precipitate proteins upon centrifugation. Also, 4-fluoro-L-phenylalanine (F-Phe; 10 µM as final concentration) was used as a recovery standard to evaluate extraction efficiency and included in the deionized water for all stool samples at this step. This mixture was vortexed for 10 min and centrifuged for 20 min at 450 g. Subsequently, the upper aqueous layer was transferred to a separate clean tube, and then the process was repeated the second time to maximize recovery of metabolites. Finally, the two stool extracts were then combined and stored at −80° C. until analysis. On the day of analysis, extracts were slowly thawed on ice and mixed with deionized water containing internal standards (10 µM), Cl-Tyr and NMS for data normalization in positive and negative ion mode detection, respectively resulting in an overall dilution of 5- and 10-fold. Pooled quality control (QC) samples were prepared from a sub-set of urine and stool extract samples (n=30 for urine, n=24 for stool) for the purpose of monitoring instrumental signal drift throughout the analysis.

Urinary and stool metabolome stability studies. Five random single-spot urine samples were collected from healthy volunteers ranging from 25 to 30 years old, including two males and three females. Each sample was placed on ice and a pooled sample was prepared within 1 hr upon initial urine collection. Aliquots of this pooled urine sample were stored at either room temperature (~22° C.) or in a fridge (4° C.) for 6, 12, 24, 36 and 48 h, which were performed in triplicate. After assigned storage duration, 1 mM sodium azide was then added and samples were stored at −80° C. prior to analysis. Six urine aliquots of a pooled urine sample were also prepared as a control and immediately transferred to a freezer at −80° C. after addition of 1 mM sodium azide. An additional three urine aliquots were transferred to the freezer without sodium azide as a negative control. The same dilution and analysis protocol as described for IBD urine samples were performed. A representative stool sample was also collected from healthy six year old twin brothers upon ethical approval from the Hamilton Integrated Research Ethics Board (Project #: 3992) and receiving a parental consent. Each stool sample was homogenized with sterile spatula and transferred into 18 tubes for different conditions in duplicates: control (−80° C. freezer), freezer (−20° C.) for 48 h, fridge (4° C.) for 2, 4, 8 and 48 h, and room temperature (~22° C.) for 2, 4, and 8 h of storage. Initial sample processing was completed within 30 min. After the assigned storage duration, samples were transferred to a freezer at −80° C. followed by lyophilisation, extraction and analysis. The same extraction protocol as freeze-dried IBD stool samples was applied in this case.

High throughput metabolite screening of urine and stool extract by MSI-CE-MS—MSI-CE-MS experiments were performed as previously described[3] on an Agilent G7100A CE system (Agilent Technologies Inc., Mississauga, ON, Canada) equipped with a coaxial sheath liquid Jetstream electrospray ion source with heated nitrogen gas to an Agilent 6550 iFunnel Q-TOF-MS system. Separations were performed using an uncoated fused silica capillary (Polymicro Technologies, AZ, USA) with an inner diameter of 50 µm, outer diameter of 360 µm, and total length of 110 cm using an applied voltage of 30 kV at 25° C. A detailed description of analytical conditions and tandem mass spectrometry (MS/MS) experimental conditions are given in the Supplemental Information. Complete lists of metabolites detected in stool and urine samples are provided in FIGS. 7 and 8, respectively. Each sample was analyzed by MSI-CE-MS under two conditions based on a background electrolyte (BGE) comprised of 1.0 M formic acid with 15% v/v acetonitrile (pH=1.80) and 50 mM ammonium bicarbonate (pH=8.50) for positive and negative ion mode detection, respectively. The sheath liquid composition for electrospray formation when using the coaxial sheath liquid interface in CE-MS was comprised of 60% v/v methanol with 0.1% v/v formic acid for analysis of cationic metabolites under positive ion mode detection, whereas 50% v/v MeOH was used as the sheath liquid for anionic metabolites under negative ion mode detection. Prior to sample injection, the capillary was conditioned with BGE for 15 min to ensure adequate equilibration. A seven serial sample injection format was used for multiplexed separations by MSI-CE-MS, which utilized an alternating hydrodynamic injection sequence of 5 s (at 100 mbar) for each sample followed by a 40 s (at 100 mbar) of BGE that served as spacer plug between each pair of diluted urine or stool extract sample. A pressure gradient was also applied during voltage application when analyzing anionic metabolites under negative ion mode detection to reduce total analysis times within 45 min, which comprised by up to 72 mbar or 7.2 kPa pressure application over 38 min (2 mbar or 0.2 kPa increase every 2-3 min).

Temporal signal pattern recognition using MSI-CE-MS was applied in this work to ensure correct sample assignment to each electropherogram peak as described elsewhere.[4] Briefly, all samples from a longitudinal study of the therapeutic effects of exclusive enteral nutrition for pediatric UC and CD patients were fully randomized and analyzed. Briefly, three samples (urine or fecal extract) were injected in duplicate and sample pairs were then diluted using a characteristic pattern within the run (i.e., 1:1, 1:2 or 2:1) to facilitate identification of sample position especially when a metabolite is not consistently detected in all samples analyzed within the same run. Additionally, a QC (i.e., pooled urine or fecal extract) was included in every run, which is essential for evaluating system stability over time resulting from non-biological experimental variation. In this case, QC was injected randomly at a position 1, 3, 5, or 7 in all runs performed by MSI-CE-MS. Q-TOF-MS was operated using full-scan data acquisition (TOF-MS mode) when performing nontargeted metabolite screening under positive and negative-ion modes over a mass range of m/z 50-1700 with an acquisition rate of 500 ms/spectrum. The ESI conditions were Vcap=3500 V, nozzle voltage=2000 V, nebulizer gas-8 psi, sheath gas=3.5 L/min at 200° C. and drying gas=16 L/min at 200° C. for both ionization modes. Furthermore, the MS voltage settings were fragmentor=120V, skimmer=65V and Oct1 RF=750 V. The Q-TOF-MS was used for collisional-induced dissociation (CID) experiments for metabolite identification when using both auto MS/MS and targeted MS/MS modes over a mass range of m/z 50-1700 with a cycle time of 3.1 s in conjunction with collisional voltages set at 10, 20 or 30V and 40 V for a precursor ion. A combination of deposited MS/MS spectral databases (e.g., HMDB),[5] in-silico fragmentation (e.g., MetFrag),[6] and manual annotation was used for MS/MS spectra interpretation.

Urinary osmolality and creatinine measurements. Osmolality was measured using Advanced Micro-Osmometer 3300 (Fisher Scientific Company). Measurement for all IBD urine samples were done in one day. Clinitrol 290 reference solution was measured intermittently every ten urine samples to ensure the accuracy of measurement. Reference solution read from 288 to 292 mOsm (actual osmolality: 290 mOsm) throughout the analysis (n=8, average reading=290 mOsm). All metabolite responses from single-spot urine samples were normalized to osmolality in order to correct for between-subject differences in hydration status. Urinary creatinine concentrations were also measured for all urine samples in this study using MSI-CE-MS. A seven-point calibration curve for creatinine was acquired in triplicate from 200 to 3000 μM with excellent linearity (R²=0.999), where the integrated peak area was normalized to an internal standard (10 μM Cl-Tyr).

Metabolomics data processing and statistical analysis. Raw data (.d format) was processed using Mass Hunter Workstation Software (Qualitative Analysis, version B.6.00, Agilent Technologies, 2012). Initial feature detection and identification was performed using Mass Hunter Molecular Feature Extractor, Molecular Formula Generator tools and an in-house compound database. Molecular features were extracted using a 10 ppm mass window and ions were annotated by their accurate mass (m/z), relative migration time (RMT) as compared to an internal standard, and ionization mode used for detection. Peak smoothing was performed using a quadratic/cubic Savitzky-Golay function (15 points) prior to peak integration. Peak areas and migration times for all molecular features and internal standards were transferred to Excel (Microsoft Office) and saved as .csv file. Finally, R program (v. 3.5.1) was used for pre-processing of the data matrix, which included calculation of relative peak area (RPA) and RMT, coefficient of variation (CV) from QC samples in every run, removal of compounds with high variance (CV>40%) from QCs, and evaluation of frequently missing compounds. Subsequently, values for each metabolite was divided by osmolality (urine) or dried weight (stool) to account for different hydration status and water content, respectively. Code for functions used for these process is freely available at https://github.com/mai-yama/DataProcess-Tools_under the name "initial_pro-cess.R". A list of authentic stool metabolites were initially curated using dilution trend filter as previously described.[3] Most univariate and multivariate data analysis was performed using Metaboanalyst 4.0,[7] including Mann-Whitney U-test, FDR adjustment for multiple hypothesis testing, principle component analysis (PCA), orthogonal partial least-squares-discriminant analysis (OPLS-DA) and receiver operating characteristic (ROC) curves. In all cases, missing values were replaced with half of the lowest detected value, whereas metabolomic data sets were (generalized) log transformed and autoscaled when performing multivariate data analysis. Also, data normality assessment and effect size calculations were performed using the Statistical Package for the Social Science (SPSS, version 21). Normality assumption was violated for majority of metabolites (88% for stool and 73% for urine) based on Shapiro-Wilk test (α=0.05). As a result, non-parametric univariate test (Mann-Whitney U-test) was also performed on untransformed metabolomics data.

Results

Cohort characteristics and inflammatory markers do not differentiate between CD and UC—Most pediatric IBD patients in this sex and age-balanced cohort (with a mean age of 13 years) were newly diagnosed cases except for three CD and four UC cases who were diagnosed within the past 3 years. Similarly, only a sub-set of IBD patients (~20%) was receiving maintenance medications at the time of sample collection as summarized in Table 1. Thus, pediatric IBD patients were largely treatment naïve without an extensive history of long-term prescribed medications and prior surgery from a single hospital site. Importantly, conventional serum and stool derived inflammatory biomarkers for IBD did not discriminate between CD and UC patients in the present study (Mann-Whitney U-test, p>0.05); however, most values were still well above the recommended threshold to be considered inactive (CRP≤1.0 mg/L, calprotectin ≤250 μg/g) clearly indicating an active inflammatory state. IBD classification and differential disease diagnosis was determined after colonoscopy together with colonic tissue biopsies collected for histopathology. Inflammation was clearly visible in all cases, further confirming an active disease state for affected children at the time of specimen collection. Overall, there were 15 (out of 19 total) matching urine and stool samples in the CD group and 8 (out of 11 total) paired samples collected from the UC group. As expected, compliance for specimen collection was greater for urine as compared to stool during clinic visits at McMaster Children's Hospital. Urine samples were aliquoted into sodium azide solution as a preservative prior to storage, whereas stool specimens were stored frozen (−80° C.) at the earliest time possible following collection. All biochemical measurements were derived from serum samples except for fecal calprotectin, whereas disease location was based on colonoscopy imaging.

TABLE 1

Summary of pediatric patient cohort who participated
in this study with clinical measurements
based on mean values and errors as ± 1 s.

| Criteria | CD (n = 19) | UC (n = 11) |
|---|---|---|
| Age; mean ± sd | 13 ± 2 | 12 ± 3 |
| Sex; male:female | 9:8 | 6:5 |
| New diagnosis (n) | 13 | 6 |
| CRP (mg/L)[a] | 40 ± 40 | 36 ± 65 |
| Fecal calprotectin (μg/g)[a] | 3360 ± 2230 | 2420 ± 1570 |
| Hemoglobin (g/L) | 107 ± 16 | 111 ± 17 |
| ESR (mm/hr) | 37 ± 21 | 35 ± 26 |
| Albumin (g/L) | 27 ± 4 | 32 ± 4 |
| Disease location (n): | | |
| Ileocolonic | 11 | NA |
| Ileocolonic + UGI | 2 | NA |
| Colonic | 3 | 11 |
| Colonic + UGI | 3 | NA |
| IBD medications at sampling: | | |
| Biologic[b] | 1 | 0 |
| Immunomodulator[c] | 1 | 0 |
| 5-ASA[d] | 0 | 3 |
| Biologic + Immunomodulator[e] | 0 | 1 |
| Urine samples available | 19 | 8 |
| Stool samples available | 15 | 11 |

Abbreviations include, CD: Crohn's disease; ESR: Erythrocyte sedimentation rate; UC: Ulcerative colitis; PCDAI: Pediatric Crohn's disease activity index; PUCAI: Pediatric ulcerative colitis activity index; UGI: Upper Gastrointestinal tract
[a]There were no significant differences (p > 0.05, Mann-Whitney U test) measured between inflammatory markers between CD and UC patients, including serum CRP and fecal calprotectin.
[b]Infliximab;
[c]Methotrexate;;
[d]Aminosalicylic Acid (ASA) or Mesalamine;
[e]Azathioprine + Adalimumab Stool extraction protocol, metabolomics data workflow and quality control—An extraction protocol for lyophilized stool specimens was optimized using pooled samples collected from IBD patients in order to ensure reliable yet quantitative analysis of fecal metabolites from gut microbes, host cells and undigested food components (i.e., nutrients, fiber). Most stool samples collected from IBD children had extremely loose consistency with frequent inclusion of blood due to active inflammation. In order to minimize biological variance, all stool samples were first lyophilized into a dried powder and then accurately weighted on an electronic balance (~15 mg) prior to extraction using pre-chilled solvents on ice at 4° C. comprised of methanol, deionized water and chloroform (4:3.6:4 ratio) based on a modified Bligh Dyer procedure as shown in FIG. 1. In this case, two consecutive aliquots of stool extracts from the upper aqueous methanol layer were combined together allowing for analysis of a wide range of polar/ionic metabolites by MSI-CE-MS with excellent technical precision (CV<10%, n=6) and recovery (>85%) while avoiding protein at the interface and lipids in the bottom chloroform layer that have deleterious effects on separation performance. In all cases, metabolite responses were normalized to an internal standard (10 μM, 4-chlorotyrosine, Cl-Tyr) and total dried stool weight (mg) in order to correct for differences in on-column injection volumes and stool heterogeneity, respectively. Additionally, blank extracts were used for authenticating metabolite signals by MSI-CE-MS with a seven sample serial injection format within a single run in order to identify reproducible (CV<40%) yet representative fecal metabolites from pooled specimens without sample carry-over effects (FIG. 1A). This process takes advantage of signal pattern recognition when encoding mass spectral information temporally within a multiplexed separation, which is needed to filter out spurious signals, background adducts and contaminant peaks that comprise the majority of signals in ESI-MS [ref]. FIG. 1(B) outlines the overall data workflow for characterization of the stool metabolome that utilizes a three-stage process for authentication with each metabolite annotated by its accurate mass, relative migration time and detection mode (m/z:RMT:mode). In addition to the initial filtering procedure applied initially on pooled stool extracts in FIG. 1(A), metabolites were included into the final data matrix provided that QC samples analyzed throughout study had adequate precision (CV<40%), and they were detected in the majority of fecal extracts from individual IBD patients (>75%). Additionally, missing values were substituted with the lowest detected ion response ratio for a metabolite in the cohort divided by two. FIG. 1(C) highlights a control chart for the recovery standard, 3-fluorophenylalanine (10 μM F-Phe) added to all stool extracts analyzed in this study under both positive and negative ion modes, which confirmed good intermediate precision (mean CV=14%, n=241) with few outliers outside warning limits (±2s). A similar strategy for molecular feature selection, data filtering, metabolite authentication and QC was also adopted for non-targeted profiling of the urine metabolome from pediatric IBD patients, which only involved a simple dilution step in deionized water prior to analysis.

Characterization of the stool and urine metabolome of pediatric IBD patients-A total of 104 fecal metabolites (66 cations, 38 anions) and 131 urinary metabolites (66 cations, 65 anions) were initially authenticated from pooled stool and urine specimens collected from pediatric IBD patients (see FIGS. 7 and 8, respectively). Overall, the majority of metabolites (>65%) were unambiguously identified after spiking with authentic standards (level 1) or putatively identified based on MS/MS spectra comparison to public databases (level 2) using reporting standards from the metabolomics standards initiative. All metabolites were annotated based on their characteristic m/z:RMT:mode together with its most likely molecular formula. However, the final metabolomics data matrix used in this study was comprised of 72 stool and 122 urinary metabolites after applying further exclusion criteria for infrequently detected metabolites (<75% in all samples) and/or compounds having poor technical precision from repeated analysis of QCs (CV>40%). Excluded compounds also comprised exogenous drugs and their metabolites based on their accurate mass and diagnostic MS/MS spectra. For instance, propofol glucuronide was detected as an exogenous drug metabolite since it was administered intravenously as a sedative anesthetic during colonscopy, whereas phenyl sulfate was a consistently measured endogenous urinary metabolite of phenylalanine catabolism. Overall, there were 50 polar/ionic metabolites consistently measured in both urine and stool samples, including amino acids and their derivatives, organic acids, amines/amino sugars and nucleosides/purines/pyrimidines. However, a majority of steroid conjugates, bile acids and other lipophilic metabolites were detected primarily in stool extracts.

Figure 2:
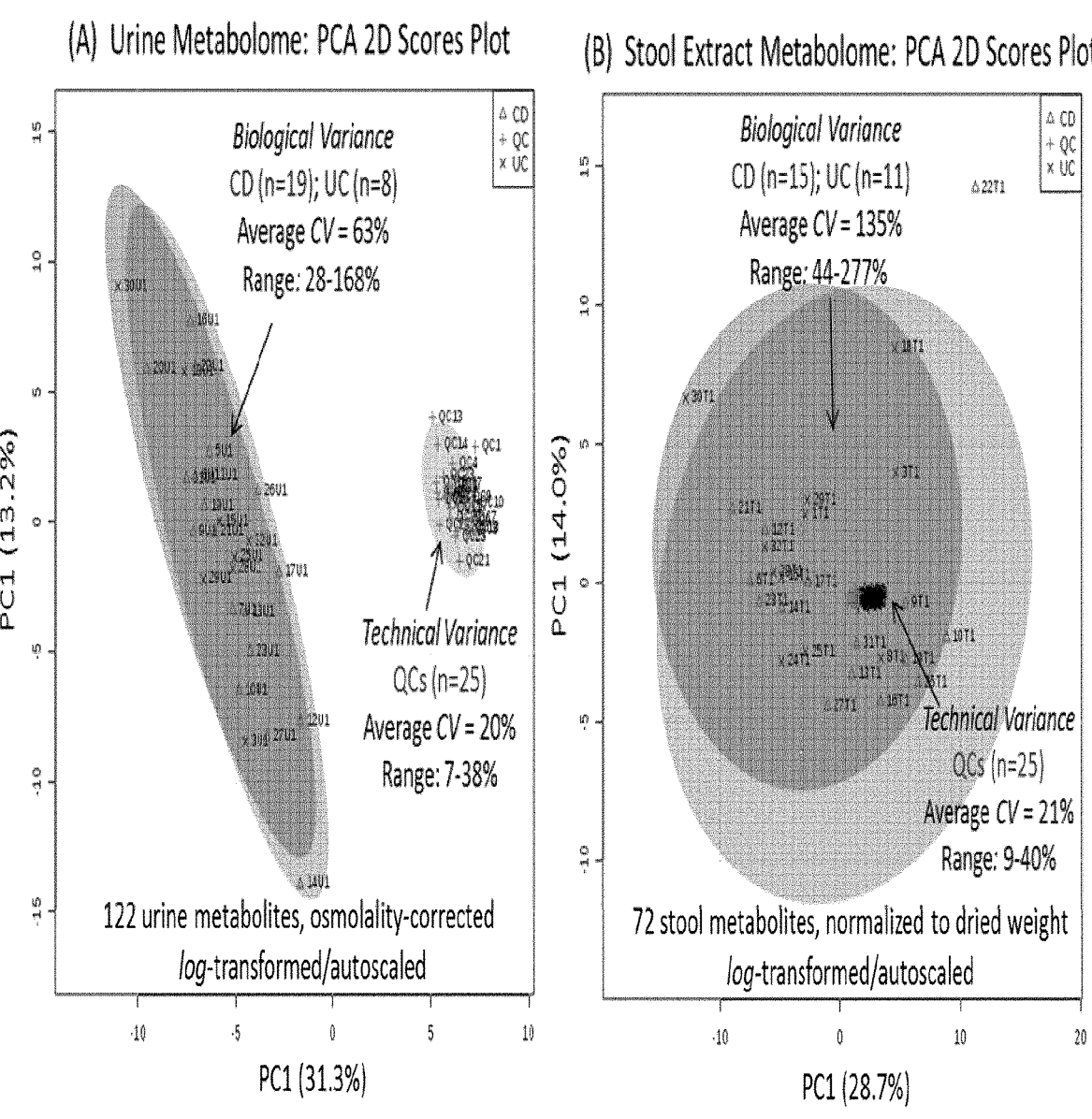
FIG. 2. A PCA 2D scores plots of (a) 122 urine metabolites from 19 CD and 8 UC patients and (b) 72 stool metabolites from 15 CD and 11 UC patients with corresponding pooled QC samples. Overall technical variance in urine and stool analysis was equivalent (CV=20%), but between-subject biological variance in stool extracts was more than two-fold larger as that of the urine metabolome. Data was normalized to sum total responses or osmolality (urine), as well as total dried weight (stool) followed by a generalized log-transformation with autoscaling.

As compared to the urine metabolome, there was a much greater extent of biological (between-subject) variance for stool metabolites among children with IBD as shown in 2D scores plots from a principal component analysis (PCA) in FIG. 2. Technical precision was effectively monitored throughout the analysis by including QC samples in a randomized order in every single run, which resulted in an average CV of 20% and 21% based on 122 urinary and 72 stool metabolites, respectively. In contrast, the average biological variance of osmolality normalized urine samples was 63%, whereas the average variability of metabolites from dried weight normalized stool extracts was 135%, reflecting the much greater heterogeneity of fecal specimens. Nevertheless, the absolute concentration of urinary metabolites is highly dependent on hydration status when relying on single-spot urine sample collection, which necessitated correction using osmolality or creatinine normalization. In this study, creatinine was not an optimal parameter for urine normalization given that the cohort comprised both male and female IBD patients, including young children and teenagers with different muscle mass and dietary patterns. Overall, urinary creatinine and osmolality measurements showed a good correlation as demonstrated by a linear regression model ($R^2$=0.610, n=27) that did not significantly impact the ranking of biomarker candidates that differentiate CD from UC.

Figure 3A:
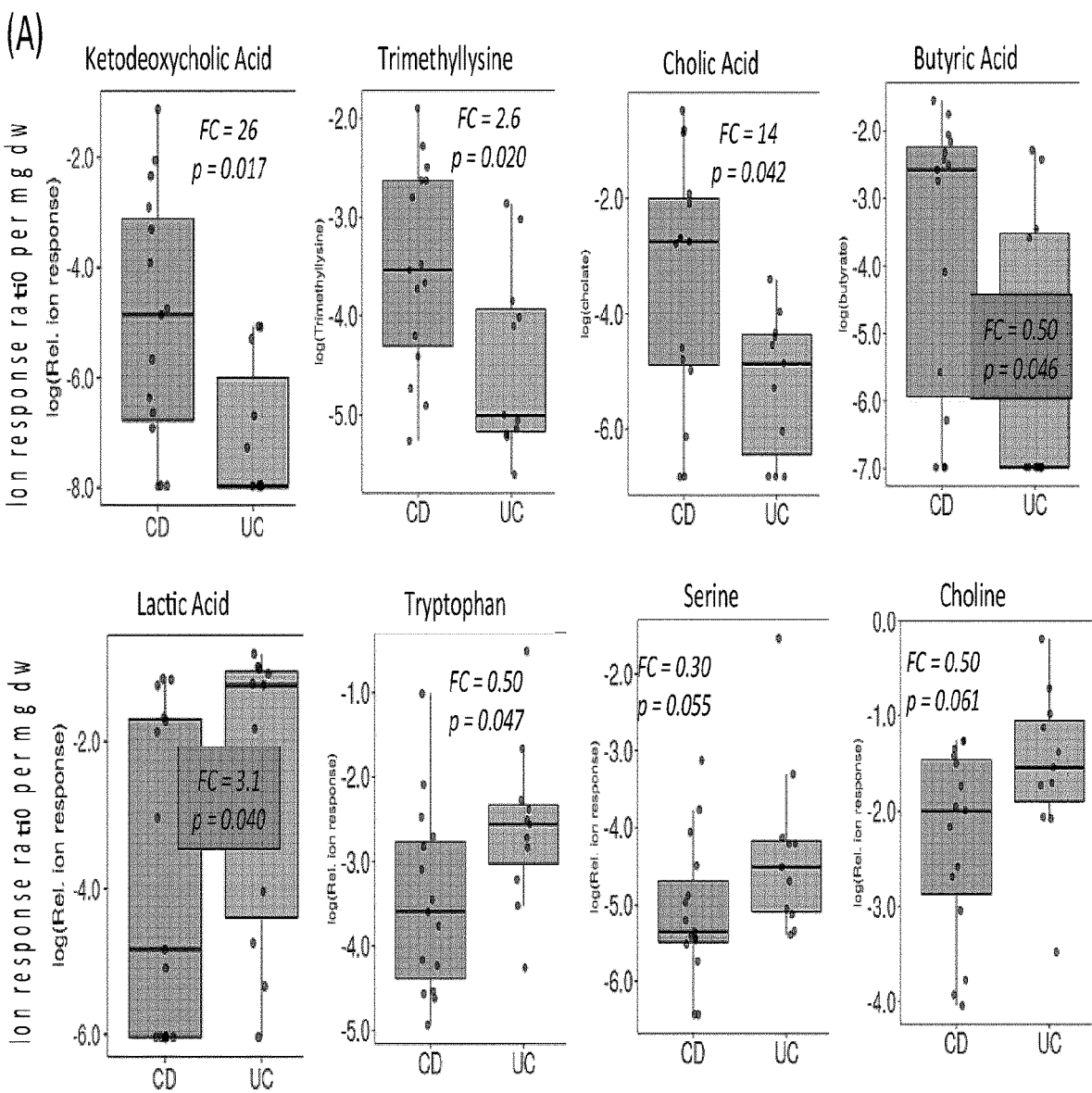
FIG. 3. (A) Box-whisker plots of metabolites differentially excreted in stool extracts (p<0.05) collected from pediatric UC (n=11) and CD (n=15) patients, where boxplots show generalized log-transformed relative ion responses. (B) ROC curves for top-ranked ratiometric and single stool metabolites differentially excreted in UC compared to CD by median fold-change (FC), Mann-Whitney U-test (p<0.05) and area under the curve (AUC). Data were normalized to dried weight for stool and no transformation was performed prior to statistical analysis.
Figure 3B:
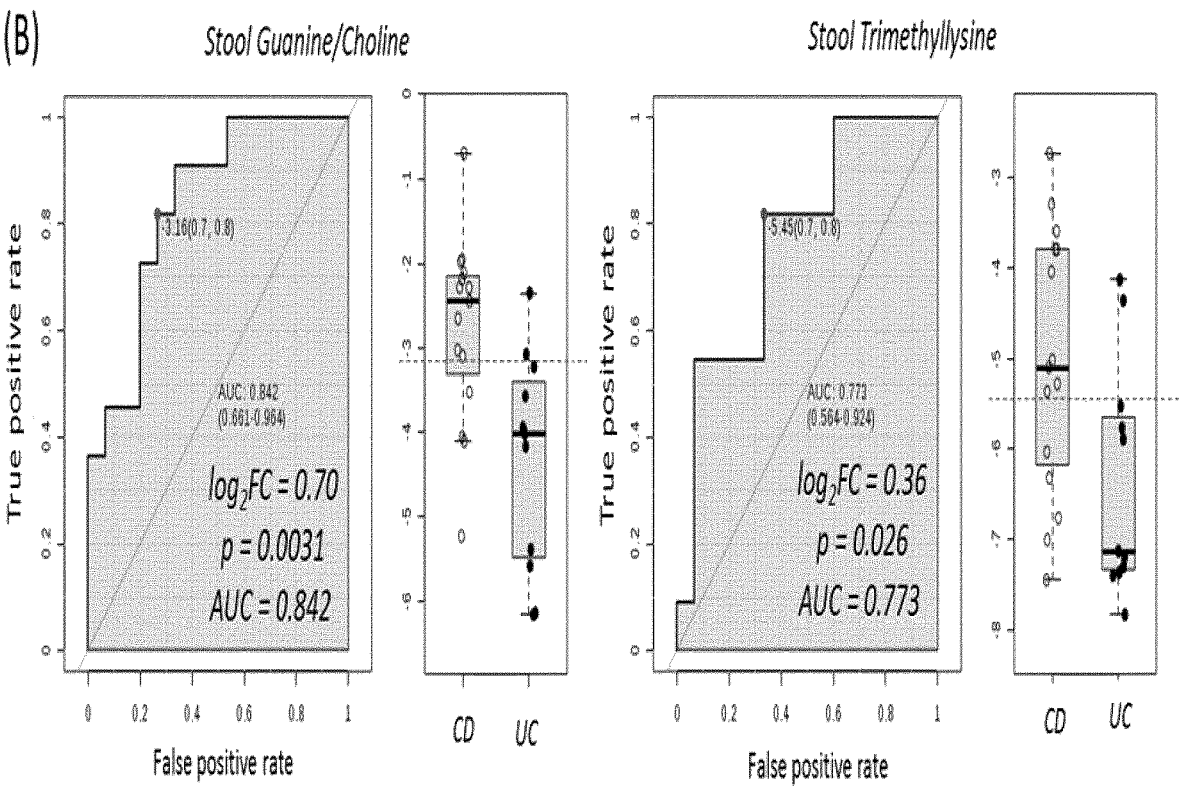

Biomarker candidates in stool and urine that differentiate CD from UC—A comparison of the stool and urine metabolome between CD and UC patients was next performed using nonparametric univariate analysis based on Mann-Whitney U-test due to skewed data distribution in the majority of metabolites (93% in stool, 70% in urine) based on a Shapiro-Wilk normality test (p<0.05). Results of univariate statistical analysis for stool metabolites are summarized in Table 2 with unadjusted p-values (<0.10), median fold-change (FC) and effect sizes.

cholic acid, deoxycholic acid, trimethyllysine and butyric acid were more abundant in stool extracts in CD patients (p<0.05). Although only marginally significant (p<0.10) with lower effect sizes (<0.40), higher excretion of serine, threonine, choline and acetylcarnitine were also apparent in stool extracts among UC patients. Due to the higher prevalence of missing compound in stool extracts, a lower 50% missing cut-off rate was applied to allow for inclusion of 7-ketodeoxycholic acid, butyric acid and lactic acid as they were largely absent (i.e., below detection limit) in stool extracts analyzed from either IBD sub-type. Box-whisker plots for the top-ranked stool metabolites that differentiate major pediatric IBD sub-types are depicted in FIG. 3, including receiver operating characteristic (ROC) curves for the top-ranked single (trimethyllysine, AUC=0.773, p=0.026) and ratiometric (guanine:choline, AUC=0.842, p=0.0031) stool derived biomarkers that discriminate CD from UC cases.

Figure 4A:
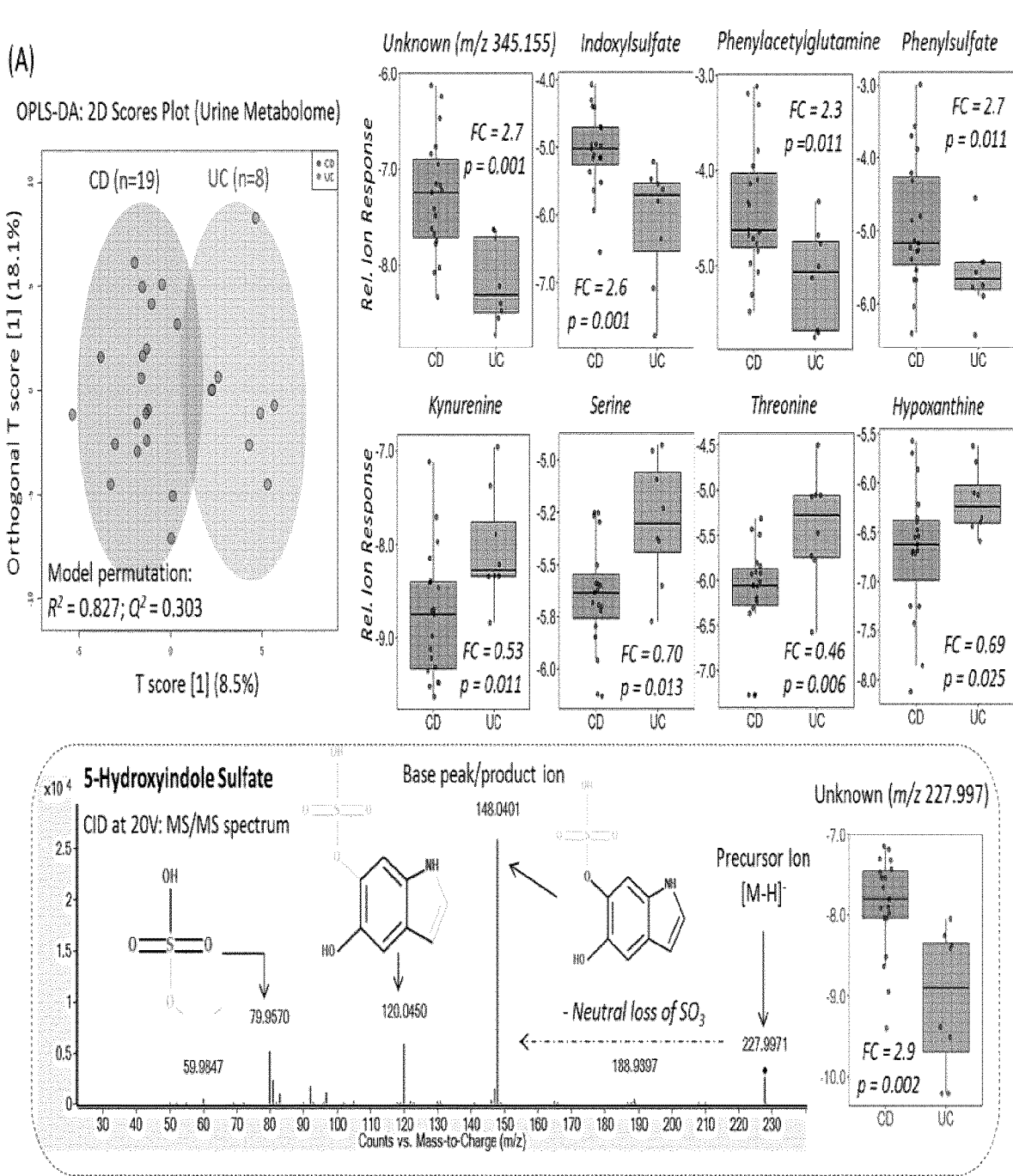
FIG. 4. (a) Overall biological variance that discriminate between UC and CD patients when projected as 2D score plot from OPLS-DA based on 122 urinary metabolites consistently detected in majority of urine samples following cross-validation ($R^2$=0.827, $Q^2$=0.303) together with box-plots of top-ranked biomarker candidates in urine (Mann-Whitney U-test, p<0.05). Unknown compound with m/z 345.155 is assigned with molecular formula of $C_{16}H_{26}O_8$ and tentatively identified as branched oxodecanoic acid. Urine metabolomics data was normalized to osmolality. Y-axis of boxplots show log-transformed relative ion response. (b) ROC curves of differentially excreted urinary metabolites ROC curves indicate the area under the curve (AUC).

A panel of putative biomarkers identified in osmolality normalized urine from IBD patients is summarized in Table 3, where CD was characterized by significantly higher excretion of tryptophan or phenylalanine catabolites as compared to UC affected children, including indoxylsulfate, phenylacetylglutamine, phenylsulfate and an unknown indole metabolite subsequently identified (level 2) as 5-hydroxy-6-indolyl-O-sulfate (FIG. 4). The MS/MS fragmentation spectrum of this oxidized indole metabolite clearly showed a production and neutral loss for sulfate resulting in formation of dihydroxyindole as the base peak (m/z 148.0401). Additionally, significantly higher levels of unknown anion (m/z:RMT, 345.1550:0.770) and cation (m/z:RMT, 222.0796:0.849) were found in CD patients. There were no database matches for these compounds, but the MS/MS fragmentation spectra were indicative of a branched oxodecanoic acid and carboxybutyl-homocysteine based on in-silico fragmentation predictions using MetFrag. Urine samples from UC patients on the other hand, contained much higher levels of amino acids, such as serine, kynurenine and hypoxanthine. These metabolites contributed to the overall separation of urinary metabolic profiles of UC and CD patients when using orthogonal partial least square-discriminant analysis (OPLS-DA) with moderate model performance following cross validation ($R^2$=0.827, $Q^2$=0.303) as shown in FIG. 4A.

TABLE 2

Top-ranked biomarker candidates from stool extracts normalized to dried mass identified by MSI-CE-MS that differentiate pediatric CD (n =15) from UC (n =11) patients.

| m/z:RMT:polarity | Chemical ID | Median FC | p-value | Effect size |
|---|---|---|---|---|
| 405.2646:0.753:n | 7-Ketodeoxycholate | 26 | 0.0173 | 0.47 |
| 189.1598:0.612:p | Trimethyllysine | 2.6 | 0.0203 | 0.45 |
| 87.0452:1.054:n | Butyric acid | 3.1 | 0.0402 | 0.41 |
| 407.2803:0.748:n | Cholic acid | 14 | 0.0423 | 0.40 |
| 89.0244:1.140:n | Lactic acid | 0.50 | 0.0464 | 0.40 |
| 205.0972:0.927:p | Tryptophan | 0.50 | 0.0472 | 0.39 |
| 391.2865:0.755:n | Deoxycholic acid | 4.3 | 0.0501 | 0.39 |
| 106.0499:0.844:p | Serine | 0.30 | 0.0554 | 0.38 |
| 104.1069:0.560:p | Choline | 0.50 | 0.0613 | 0.37 |
| 120.0655:0.887:p | Threonine | 0.40 | 0.0619 | 0.37 |
| 204.123:0.792:p | Acetylcarnitine | 0.60 | 0.0862 | 0.34 |

* Statistical significance based on Mann-Whitney U-test, p < 0.10 with a median FC > 2.0 or <0.5, where a 50% missing rate was applied to allow inclusion of more differentially excreted stool metabolites.

Despite the large biological variability observed in the stool metabolome, clear trends in bile acids, short-chain fatty acids and certain amino acids were found when comparing differential excretion patterns of CD and UC patients. For instance, UC was characterized by a higher excretion of tryptophan and lactic acid, whereas ketodeoxycholic acid,

TABLE 3

Top-ranked biomarker candidates from osmolality-normalized urine identified by MSI-CE-MS that differentiate pediatric CD (n = 19) from UC (n = 8) patients.

| m/z: RMT:polarity | Chemical ID | Median FC | p-value | Effect size |
|---|---|---|---|---|
| 212.0023:1.025:n | Indoxylsulfate | 2.55 | 1.18 E−03 | 0.59 |
| 345.1553:0.770:n | Unknown fatty acid, $C_{16}H_{26}O_8$ | 2.68 | 1.18 E−03 | 0.59 |
| 106.0499:0.868:p | Serine | 0.70 | 1.33 E−02 | 0.47 |
| 227.9968:0.979:n | 5-Hydroxyindole sulfate | 2.76 | 1.89 E−03 | 0.60 |
| 120.0652:0.905:p | Threonine | 0.46 | 6.21 E−03 | 0.53 |
| 209.0921:0.887:p | Kynurenine | 0.53 | 0.0112 | 0.48 |
| 263.1037:0.826:n | Phenylacetylglutamine | 2.34 | 0.0112 | 0.48 |
| 172.9912:1.135:n | Phenylsulfate | 2.67 | 0.0217 | 0.44 |
| 137.0457:1.039:p | Hypoxanthine | 0.69 | 0.0253 | 0.43 |
| 222.0796:0.849:p | 5-(δ-carboxybutyl)homocysteine | 2.76 | 0.0253 | 0.43 |
| 350.0880:0.788:n | Indole-3-acetate glucuronide | 2.18 | 0.0293 | 0.42 |
| 104.0706:0.940:p | Dimethylglycine | 0.66 | 0.0463 | 0.39 |

* Statistical significance determined by a Mann-Whitney U-test, p < 0.05

Figure 4B:
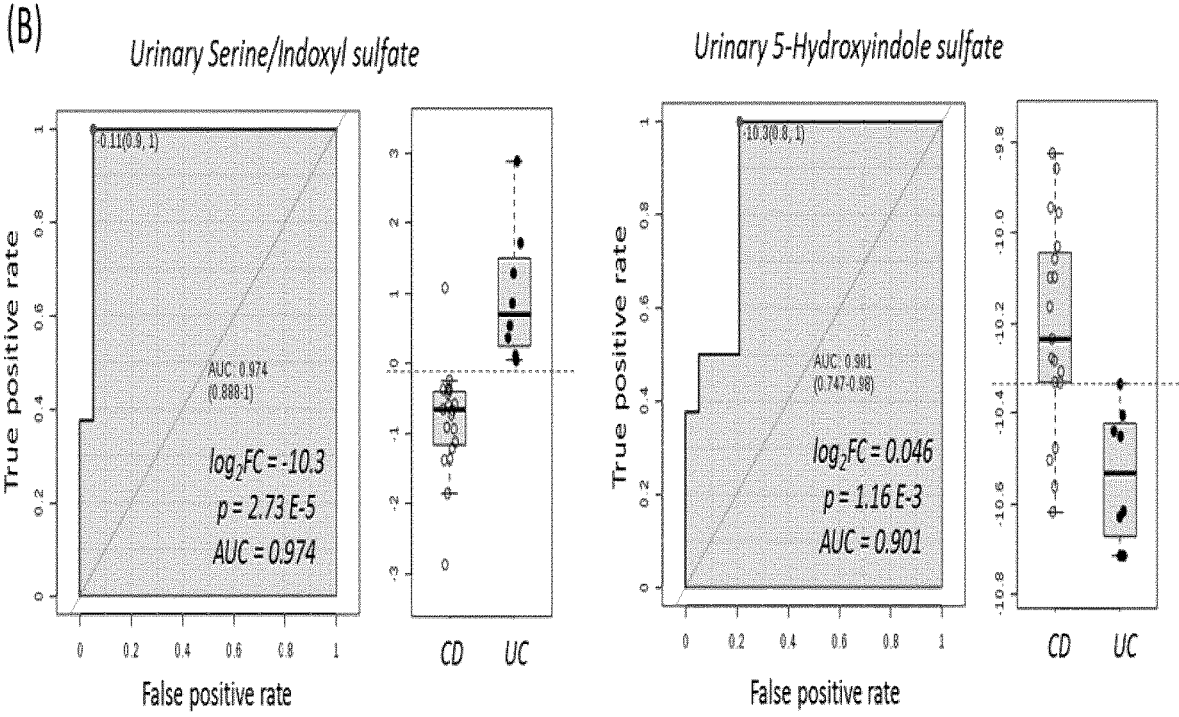

Moreover, these same urinary metabolites remained significant when using a univariate Mann-Whitney U-test (without data transformation) after adjustment for multiple hypothesis testing using Benjamini-Hochberg FDR adjustment (q<0.05) with moderate effect sizes of 0.50 to 0.60. Ratio metric analysis also uncovered a correlative relationship between kynurenine and indole derived metabolites, which are all derived from the catabolism of tryptophan. Specifically, the ratio of serine to indoxylsulfate achieved an AUC=0.967 and p=2.73 E$^{-5}$ as reflected by a sensitivity of 100% and a specificity of 95% (FIG. 4B). Similarly, osmolality normalized urinary 5-hydroxyindole sulfate also showed very good discriminating performance with an AUC=0.901 and p=1.16 E-3 with a sensitivity of 100%, but with a lower specificity of 79%.

Chemical stability of lead urinary and fecal biomarkers with delayed storage—To investigate the effect of different storage conditions and other pre-analytical factors that may affect results, the impacts of delayed storage and storage temperature were studied systematically with representative urine and fecal samples collected from healthy volunteers. Both subjects who provided stool samples were 6-year-old twin boys. Despite the same diet, bile acids and butyrate had an opposite trend of changes between the twins, while amino acids and choline generally increased with longer storage duration at room temperature in both subjects, which may indicate differences in microbial metabolism of butyrate and bile acids. Overall, greater changes in stool metabolite levels were observed at room temperature as expected from the higher microbial activities at warmer temperatures; however, storage of stool samples under refrigeration did not prevent alteration in metabolite levels after as short as 2 hr as seen in ketodeoxycholate and trimethyllysine. Furthermore, freeze-thaw cycle by storing samples in a freezer for 48 h and thawing at room temperature affected the stability of the majority of stool metabolites to a greater extent than a 48 h storage at room temperature or under refrigeration. In contrast to the variable stability observed among stool metabolites, urinary indole and phenolic metabolites were remarkably stable under different storage conditions, however amino acids were found to significantly decrease at room temperature within 6 h. The decreasing trends observed in hypoxanthine, kynurenine, serine and threonine may indicate oxidation or biotic degradation of these compounds at room temperature, which was effectively prevented when urine samples were stored at 4° C. Furthermore, the addition of sodium azide as a preservative did not perturb metabolite responses analyzed based on the comparison with control values.

DISCUSSION

The present study focused on pediatric IBD. Higher excretion of amino acids, particularly serine and threonine in urine and stool of UC were found as compared to the same samples from CD patients, indicating altered amino acid metabolism and subsequent development of autoimmunity. In addition to serine and threonine, UC patients were characterized by higher excretion of metabolites in purine metabolism and key metabolite for DNA synthesis, namely hypoxanthine in urine and choline in stool. On the other hand, guanine, a nucleic acid in purine pathway, was found more enriched in stool of CD patients.

Samples from CD patients were characterized by remarkable increase in bacterial metabolites such as indole and phenolic compounds in urine, and trimethyllysine and bile acids in fecal samples. In addition to cholate, other bile acids were also elevated in feces of CD patients in this study indicating the overall increase of unabsorbed bile acids compared to UC patients who lack disease involvement in their ileum. High excretion of trimethyllysine by CD patients was also observed.

Urinary indole and phenolic sulfates that were abundant in urine of CD patients. High urinary excretion of kynurenine by UC patients observed in this study perhaps indicates IDO-mediated dysregulation of immune response more likely taking place in UC than CD patients. Conversely, significantly higher urinary excretion of indole metabolites in CD patients indicates increased conversion of tryptophan to indole through bacterial enzyme, tryptophanase, which consequently leaves less tryptophan available for kynurenine, as well as serotonin production.

This study is the first to report significant increase in urinary excretion of indoxylsulfate, phenol sulfate and other indole compounds in CD.

Figure 6:
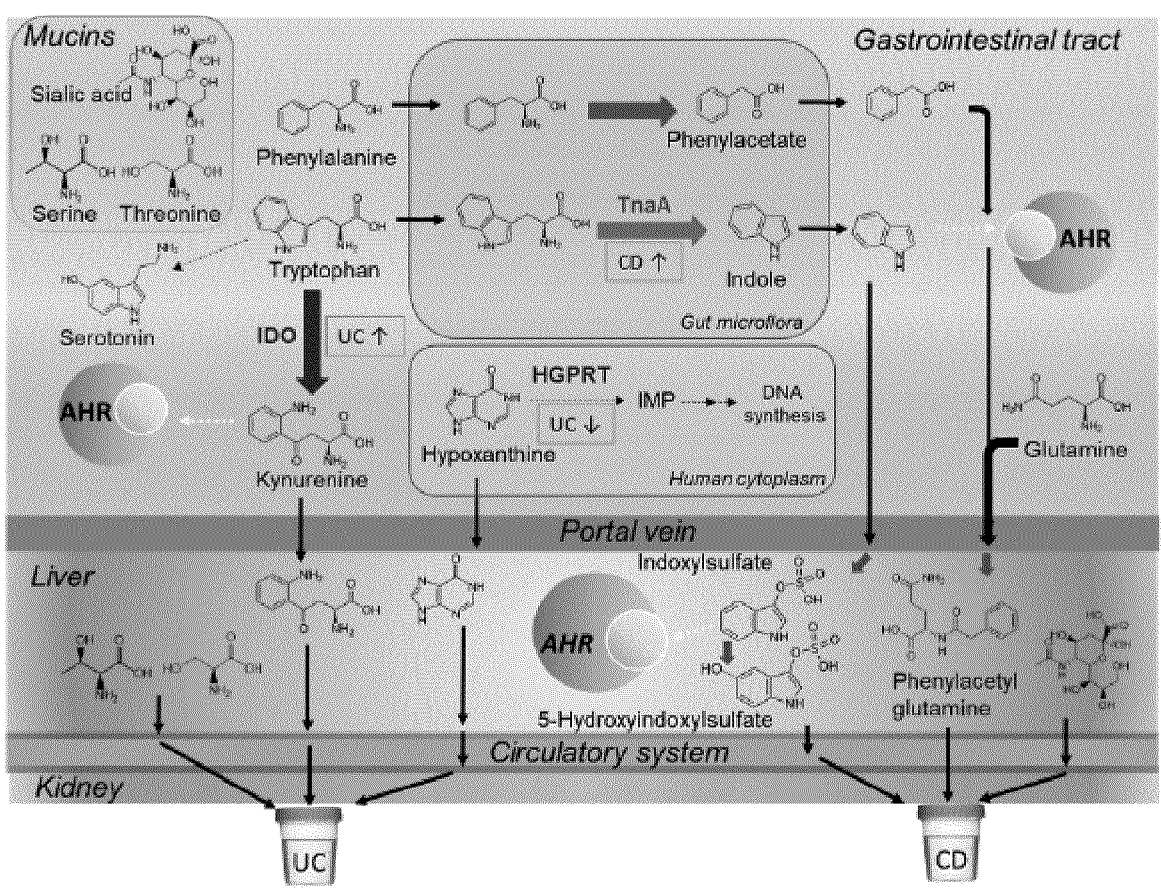
FIG. 6. Proposed metabolic pathways associated with lead biomarker candidates identified in urine. Thick arrows represent enzymatic conversions and dotted arrow represent binding to AHR. AHR: Aryl hydrocarbon receptor; IDO: indoleamine 2, 3-dioxygenase; TnaA: Tryptophanase, HGPRT: hypoxanthine-guanine phosphoribosyltransferase.

These findings suggest novel perspectives on pathological mechanisms behind IBD that are distinct between CD and UC. Proposed metabolic pathways associated with lead biomarker candidates identified in urine are shown in FIG. 6. In short, presence of opportunistic pathogens, concurrent intestinal mucus depletion, impaired mucosal barrier function, and overexpression of enzyme capable of producing AHR ligands may play a central role in immune activation in UC patients while increased production of potentially toxic bacterial metabolites in the liver, kidney and circulatory system may contribute particularly to extra-intestinal symptoms of CD patients. Additionally, defects in cell proliferation to re-gain mucosal barrier function was implicated in both groups with involvement of different substrates for the enzyme, HGPRT, in purine pathway.

Example 2

Further work was conducted to determine additional biomarkers related to UC/CD and monitoring of EEN therapy.

Pediatric IBD study cohort. This study was approved by the Hamilton Integrated Research Ethics Board (#15-365) and parental consent was obtained for all the participants. The study enrolled children from 5 to 18 years old who had been diagnosed with IBD by endoscopy, histology and radiography at McMaster Children's Hospital. Patients were included if they were admitted to hospital to be initiated on EEN therapy (Peptamen® 1.5 at 120% of their daily caloric needs), or intravenous CS (1 mg/kg/day methylprednisolone) for induction of IBD remission. Patients were discharged home once full volumes of EEN feeds administered via a nasogastric tube were achieved (<72 h upon admission), and other than formula, they were allowed to consume only clear fluids orally. Patients on CS therapy were discharged home once symptoms improved in the hospital, when they were transitioned to oral prednisolone while maintaining their normal diet throughout the intervention. Patients were excluded if they were younger than 5 years, received antibiotic therapy, or did not require admission to hospital. None of these patients have undergone resection surgery. Clinical improvement was defined as a decrease in the Pediatric Crohn's disease activity index (PCDAI) or modified Pediatric ulcerative colitis activity index (PUCAI) from baseline enrolment, and clinical remission was defined as a score of ≤10 in each scale. Active disease was defined as all baseline clinical, and biochemical (CRP, albumin, hemoglobin, FCP) parameters. Remission was defined as clinical remission and biochemical markers within normal limits (e.g., CRP≤1 mg/L; FCP≤250 mg/g). Response to treatment, but not clinical remission was defined as improvement in disease activity scores, and biochemical parameters from active disease, whereas no response was defined as a worsening of disease symptoms from baseline. Further details on this longitudinal study to evaluate of the efficacy of EEN and CS treatment on pediatric IBD patients are described elsewhere.[24]

Urine sample collection, storage, and workup procedure. All urine samples included in this study were collected prior to and following induction therapy (i.e. EEN or CS) at McMaster Children's Hospital. Single-spot urine samples were collected randomly in the morning. Following collection, 1.0 mM of sodium azide was added to all urine samples as an antimicrobial preservative and then samples were stored in a fridge before being transferred to a freezer at −80° C. All urine samples (25 μL aliquot) were thawed slowly on ice and then diluted (from 5 to 10-fold) in ultra-grade LC-MS water containing two internal standards, 3-chloro-L-tyrosine (Cl-Tyr, 10 μM) and sodium 2-naphthalenesulfonate (NMS, 10 μM), which was followed by mixing using a vortex for 30 s. Pooled quality control (QC) samples were prepared from a random sub-set of all urine samples (n=30) for assessment of technical precision and long-term instrumental signal drift. Urine samples were collected at baseline (n=28) and following treatment interventions (n=67) from pediatric CD and UC patients over an eight week period; however, urine samples were not provided consistently at every time point by all participants, and one patient later dropped out of the clinical trial. Osmolality was measured using Advanced Micro-Osmometer 3300 (Fisher Scientific Company), and urinary creatinine was measured by MSI-CE-MS that was linearly correlated to urine osmolality.

Urinary metabolome stability studies. Five random single-spot urine samples were collected from five healthy volunteers for metabolite stability studies. Each sample was placed on ice and a pooled sample was prepared within 1 h upon initial urine collection. Aliquots of this pooled urine sample were stored at either room temperature (~22° C.) or in a fridge (4° C.) for 6, 12, 24, 36 and 48 h. After assigned storage duration/temperature, 1.0 mM sodium azide was then added and samples were then stored at −80° C. with each sample performed in triplicate. Six urine aliquots of a pooled urine sample were also prepared and immediately transferred to a freezer at −80° C. with or without 1.0 mM sodium azide as controls. The same dilution and analysis protocol were performed when using MSI-CE-MS as described for pediatric IBD urine samples.

Nontargeted metabolite screening of urine by MSI-CE-MS. MSI-CE-MS experiments were performed on an Agilent G7100A CE system (Agilent Technologies Inc., Mississauga, ON, Canada) equipped with a coaxial sheath liquid Jetstream electrospray ion source with heated nitrogen gas to an Agilent 6550 iFunnel Q-TOF-MS system. Separations were performed using an uncoated fused silica capillary (Polymicro Technologies, AZ, USA) with an inner diameter of 50 μm, outer diameter of 360 μm, and total length of 110 cm with a voltage of 30 kV at 25° C. Each diluted urine sample was analyzed by MSI-CE-MS under two conditions based on a background electrolyte (BGE) comprised of 1.0 M formic acid with 15% vol acetonitrile (pH=1.80) and 50 mM ammonium bicarbonate (pH=8.50) when using positive (i.e., basic/zwitterionic metabolites) and negative (i.e., acidic metabolites) ion mode detection, respectively. The sheath liquid composition for electrospray formation when using the coaxial sheath liquid interface in MSI-CE-MS was comprised of 60% vol methanol with 0.1% vol formic acid under positive ion mode detection, and 50% vol MeOH under negative ion mode detection with full-scan data acquisition over a mass range of m/z 50-1700. Prior to sample injection, the capillary was conditioned with BGE for 15 min to ensure adequate equilibration. A seven sample serial injection format was used in MSI-CE-MS for multiplexed separations of urine samples, which utilized an alternating hydrodynamic injection sequence of 5 s (at 100 mbar) for each sample followed by a 40 s (at 100 mbar) of BGE that served as spacer plug between each pair of diluted urine sample. Briefly, all urine samples (n=95) collected from a longitudinal study of pediatric IBD patients in both EEN and CS treatment arms were fully randomized for analysis as a single batch. Three urine samples were introduced in duplicate in each run by MSI-CE-MS, where sample pairs are diluted using a distinctive injection pattern (i.e., 1:1, 1:2 or 2:1) to facilitate identification of exact sample position via temporal signal pattern recognition as previously described (DiBattista et al. J Protome Res. 2019; 18:841-854). Also, a QC (i.e., pooled urine) as a seventh sample was introduced in a random position in every run, which enables robust correction of inter-batch effects as required for longitudinal and/or large-scale metabolomic studies. The ESI conditions were Vcap=3500 V, nozzle voltage=2000 V, nebulizer gas=8 psi, sheath gas-3.5 L/min at 200° C. and drying gas=16 L/min at 200° C. for both ionization modes. Also, the MS voltage settings were fragmentor=120V, skimmer-65V and Oct1 RF=750 V. Structural elucidation of unknown urinary metabolites was performed by collisional-induced dissociation when using auto MS/MS and targeted MS/MS modes on a QTOF-MS system with collision energies at 10, 20 or 30V and 40 V. A combination of deposited MS/MS spectral databases (e.g., HMDB), in-silico fragmentation (e.g., MetFrag), and manual annotation was used for MS/MS spectral interpretation previously applied to identify urinary biomarkers associated with IBS (Yamamoto et al. Metabolomics. 2019; 15:82).

Metabolomics data processing and statistical analysis. Raw data (.d format) was processed using Mass Hunter Workstation Software (Qualitative Analysis, version B.6.00, Agilent Technologies, 2012). Initial molecular feature detection and metabolite identification was performed using Mass Hunter Molecular Feature Extractor, Molecular Formula Generator tools and an in-house compound database. Molecular features were extracted using a 10 ppm mass window and ions were annotated by their accurate mass (m/z), relative migration time (RMT) as compared to an internal standard (Cl-Tyr or NMS), and ionization mode (m) used for detection (p: positive; n: negative). Peak smoothing was performed using a quadratic/cubic Savitzky-Golay function (15 points) prior to peak integration. Peak areas and migration times for all molecular features and internal standards were transferred to Excel (Microsoft Office) and saved as .csv file. Next, determination of relative peak area (RPA) and RMT, and coefficient of variation (CV) from QC samples in every run was calculated, where urinary metabolites with high technical variance (CV>35%), low detection frequency (<75%) or exogenous compounds from drug administration were excluded from the final data matrix. Subsequently, ion responses for authentic urinary metabolites consistently measured in most urine samples were normalized to osmolality or preferably normalized to the sum of all urinary metabolite responses by MSI-CE-MS to adjust for differences in hydration status. Multivariate data analysis was performed using Metaboanalyst 4.0, including principle component analysis (PCA), partial least-squares-discriminant analysis (PLS-DA) and receiver operating characteristic (ROC) curves. In all cases, missing values were replaced with half of the lowest detected value, whereas metabolomic data sets were (generalized) log transformed and autoscaled unless otherwise stated. Also, data normality and effect size calculations were performed using the Statistical Package for the Social Science (SPSS, version 21). Normality assumption was violated for majority (73%) of urinary metabolites based on Shapiro-Wilk test ($\alpha=0.05$). As a result, non-parametric univariate test (Mann-Whitney U-test) was performed on the sum normalized urine metabolomic data matrix for differentiation of IBD sub-types at baseline. A repeat measures 2-way analysis of variance (ANOVA, interaction effect, treatment×time) on log-transformed and sum normalized data sets was performed to identify urinary biomarkers associated with EEN as compared to CS induction therapy using matching/repeat urine samples collected after 2 and 4 weeks from baseline for each IBD patient. Urinary metabolic trajectories were also plotted for individual IBD patients over the eight week intervention period for EEN and CS treatment arms.

Results

Study population and pediatric IBD characteristics— Most pediatric IBD patients (n=28) in this sex and age-balanced cohort (mean age of 13 years) were newly diagnosed cases (~73%) except for 8 cases who were diagnosed within 3 years of recruitment. Similarly, only a sub-set of IBD patients (~20%) was receiving maintenance medications at the time of sample collection as summarized in Table 4.

TABLE 4

Pediatric IBD patients who participated in this intervention study with clinical measurements based on mean values and errors as ± 1 s. All biochemical measurements were derived from serum or urine samples except stool for FCP, whereas disease location was based on colonoscopy imaging.

| Criteria | CD (n = 18) | UC (n =8) |
|---|---|---|
| Age | 13 ± 2 | 12 ± 3 |
| Sex; male:female | 9:8 | 6:5 |
| New diagnosis (%) | 13 (72%) | 6 (75%) |
| EEN; CS treatment arm (n) | 15; 3 | 1; 7 |
| CRP (mg/L)[a] | 40 ± 40 | 36 ± 65 |
| Fecal calprotectin (µg/g)[a] | 3240 ± 2210 | 2558 ± 1150 |
| Hemoglobin (g/L) | 109 ± 18 | 110 ± 16 |
| ESR (mm/hr) | 37 ± 26 | 43 ± 23 |
| Albumin (g/L) | 28.2 ± 4.8 | 30.4 ± 2.3 |
| WBC (x $10^9$/L) | 8.1 ± 2.3 | 7.3 ± 2.0 |
| Urinary creatinine (mg/L) | 11.0 ± 5.2 | 9.1 ± 6.6 |
| Urine osmolality (mOsm/kg) | 480 ± 190 | 408 ± 250 |
| Disease location (n): | | |
| Ileocolonic | 11 | NA |
| Ileocolonic + UGI | 2 | NA |
| Colonic | 2 | 8 |
| Colonic + UGI | 3 | NA |
| Maintenance medications:[b] | | |
| Biologic | 1 (2) | 0 (0) |
| Immunomodulator | 2 (10) | 0 (0) |
| 5-ASA | 0 (2) | 1 (5) |
| Biologic + Immunomodulator | 2 (2) | 1 (2) |
| Clinical outcomes:[c] | | |
| Remission; Response; No response | 11; 7; 0 | 4; 1; 2 |

[a]There were no significant differences (p > 0.05, Mann-Whitney U test) measured between serological, stool and urine markers between CD and UC patients, including serum CRP and FCP.
[b]Maintenance medications prior to and (after) ENN or CS therapy, including Biologics: Adalimumab/Humira ® or Infliximab/Remicade ®; Immunomodulators: Methotrexate or Azothioprine/Imuran ®; 5-ASA: Aminosalicylic Acid or Mesalamine/Pentasa ®; and Combination Biologics: Adalimumab + Azathioprine or Methodextrate
[c]Clinical improvement was defined as a decrease in the PUCAI or modified PCDAI from baseline enrolment, and clinical remission was defined as a score of <10 in each scale. Remission was defined as clinical remission and biochemical markers within normal limits (FC < 250 µg/g).
Abbreviations include, CD: Crohn's disease; ESR: Erythrocyte sedimentation rate; FCP: fecal calprotectin; UC: Ulcerative colitis; PCDAI: Pediatric Crohn's disease activity index; PUCAI: Pediatric ulcerative colitis activity index; UGI: Upper gastrointestinal tract. One UC patient dropped out during the clinical intervention study.

Thus, IBD affected children were largely treatment naïve without an extensive history of long-term medication use and prior surgery. Importantly, serum and stool inflammatory biomarkers for IBD do not discriminate between CD and UC patients due to large between-subject variability (Mann-Whitney U-test, p>0.05); however, most values were well above the recommended threshold to be considered active flaring conditions (CRP≥1.0 mg/L, FCP≥250 µg/g). As a result, IBD classification and differential disease diagnosis was determined after colonoscopy together with colonic tissue biopsies collected for histopathology. Inflammation was clearly visible in all cases, further confirming an active disease state for participants upon recruitment. As expected, CD patients were more heterogeneous since the site of inflammation can occur along the entire digestive tract, but most often in ileal and colonic region with transmural inflammation. In contrast, for UC patients, inflammation was typically confined to the mucosal and submucosal layers of the colon. Also, most pediatric IBD patients achieved full clinical remission (~56%) or a positive treatment response with lower inflammation (~30%) from baseline following 8 weeks of EEN or CS therapy administered mainly to CD and UC children, respectively. Since EEN is the recommended treatment option for newly diagnosed pediatric CD, few families consented to CS therapy (and vice-versa) as EEN still lacks clinical evidence of efficacy to induce UC remission.

Urine metabolome of pediatric IBD patients and metabolite authentication—A targeted and nontargeted approach was used for characterization of the urine metabolome from pediatric IBD patients when using MSI-CE-MS, which offers a high throughput platform for global analysis of polar/ionic metabolites with minimal sample workup. A dilution trend filter was initially used for selecting consistently measured metabolites from a pooled urine sample by MSI-CE-MS (CV<15%, no blank signal) while rejecting spurious ions, degenerate signals, and background compounds that constitute that majority of molecular features in ESI-MS.[25] Mean responses for all urinary metabolites were normalized to an internal standard, and they were annotated based on their characteristic accurate mass, relative migration time and detection mode (m/z:RMT:mode). A total of 132 urinary metabolites (66 cations, 66 anions) were initially authenticated, and the majority (>65%) were unambiguously identified after spiking with authentic standards (level 1), putatively identified based on MS/MS spectral comparison to public databases (level 2) or annotation of MS/MS spectra (level 3) when reference spectra are lacking. However, a final list of 122 urinary metabolites were considered after excluding infrequently detected metabolites (<75% of all urine samples) and/or compounds with poor technical precision as measured in repeat QC samples (CV>35%). Many rejected ions included over-the-counter drugs and their metabolites (e.g., acetaminophen sulfate, salicyluric acid) that were confirmed based on their accurate mass and/or diagnostic MS/MS spectra. For instance, urinary propofol glucuronide was identified (level 3) as an exogenous drug metabolite since it was administered intravenously as a sedative anesthetic during colonscopy at baseline together with hydroxypropofol glucuronide. Similarly, urinary mesalamine or 5-aminosalicylic acid (5-ASA) was detected in only a sub-set of IBD patients who were prescribed this maintenance medication prior to recruitment due to its immunosuppressant and anti-inflammatory activities. In contrast, phenyl sulfate is an endogenous urinary metabolite retained in the final data matrix since it is measured consistently with good technical precision in most urine samples.

Biomarker candidates in urine that differentiate pediatric CD from UC-A comparison of the urine metabolome between CD and UC affected children at baseline was next performed using complementary multivariate and univariate data analysis. 10 urinary metabolites were found to consistently differentiate CD from UC children based on either sum (Table 5) or osmolality normalized data when using a Mann-Whitney U-test (p<0.05).

TABLE 5

Top-ranked urinary biomarkers (sum-normalized) identified by MSI-CE-MS that differentiate pediatric CD (n = 18) from UC (n = 8) patients prior to induction therapy.

| m/z:RMT:mode | Metabolite ID; HMDB# | Median FC | p-value | Effect size |
|---|---|---|---|---|
| 212.002:1.025:n | Indoxyl sulfate; HMDB0000682 | 2.03 | 0.00111 | 0.443 |
| 120.065:0.905:p | Threonine; HMDB0000167 | 0.51 | 0.00485 | 0.345 |
| 345.155:0.770:n | Unknown fatty acid; $C_{16}H_{26}O_8$ | 1.93 | 0.00737 | 0.309 |
| 106.050:0.868:p | Serine; HMDB0000187 | 0.74 | 0.0122 | 0.273 |
| 308.099:0.791:n | Sialic acid; HMDB000230 | 1.89 | 0.0122 | 0.254 |
| 263.104:0.826:n | Phenylacetylglutamine; HMDB00006344 | 1.92 | 0.0144 | 0.261 |
| 137.046:1.039:p | Hypoxanthine; HMDB0000157 | 0.54 | 0.0144 | 0.178 |
| 222.080:0.849:p | 5-(δ-Carboxybutyl)homocysteinea | 0.44 | 0.0198 | 0.239 |
| 209.092:0.887:p | Kynurenine; HMDB0000684 | 0.61 | 0.0268 | 0.204 |
| 227.997:0.979:n | 5-Hydroxyindole sulfate[a] | 1.87 | 0.0357 | 0.210 |

* Statistical significance determined by a Mann-Whitney U-test, p < 0.05 with effect size calculated using ($Z^2$/N-1).
[a] Putative identification (level 2) of unknown metabolites based on experimental/in silico MS/MS and mobility.

In a panel of discriminating urinary metabolites from recently diagnosed IBD children, CD is characterized by higher excretion of tryptophan or phenylalanine catabolites as compared to UC, including indoxylsulfate, phenylacetyl-glutamine, and an unknown indole metabolite subsequently identified (level 3) as 5-hydroxyindoxyl-3-O-sulfate. The MS/MS fragmentation spectrum of this unreported oxidized indole metabolite clearly shows a neutral loss for sulfur trioxide (m/z 79.957) with formation of dihydroxyindole as the base peak/product ion (m/z 148.0401). As expected, hydroxyindoxyl sulfate was also strongly correlated with urinary indoxyl sulfate (r=0.594, n=97) from pediatric IBD patients while having about a 15-fold lower median abundance. Also, urinary sialic acid (N-acetylneuraminic acid) and a singly charged unknown anion (345.155:0.770:n; $C_{16}H_{26}O_8$) was higher in CD as compared to UC children, which was putatively identified as a modified dicarboxylic acid. On the other hand, UC children excreted higher levels of serine, threonine, kynurenine, hypoxanthine, and an unknown sulfur-containing singly charged cation (222.078:0.849:p, $C_8H_{15}NO_4S$) tentatively identified (level 3) as carboxybutylhomocysteine that was correlated (r=0.566) with urinary hypoxanthine. However, authentic standards were unavailable for direct spiking preventing unambiguous structural elucidation of these unknown ions, including their exactstereochemistry. Nevertheless, urinary serine: indoxyl sulfate and serine: hydroxyindole sulf ate were optimal ratiometric biomarkers for discriminating between the two major IBD sub-types when using receiver operating characteristic (ROC) curves with good accuracy (AUC~0.960-0.970, p<3.00 E-5) as compared to indoxyl sulfate alone (AUC=0.910, p=1.60 E-3). Urine stability studies were also performed in this study, which revealed that indoxyl sulfate, hydroxyindoxyl sulfate and certain other urinary metabolites can tolerate delays to storage for up to 48 h even at room temperature without evidence of degradation/biotransformation. In contrast, other urinary metabolites (e.g., serine, threonine, hypoxanthine, kynurenine) were stable for up to 48 h if kept refrigerated (+4° C.) prior to freezing (-80° C.). As expected, the addition of sodium azide (1.0 mM) as a preservative in all urine samples did not alter metabolite responses as compared to untreated urine samples (p>0.05).

Specific urinary biomarkers following EEN or CS therapy of IBD children—Therapeutic responses for individual IBD children to induction therapy was assessed via clinical and/or biochemical indicators based on a PCDAI/PUCAI score≤10 or a serum CRP (≤1 mg/L) and FCP (≤250 μg/g) under threshold values associated with remission or mucosal healing as compared to active inflammation at baseline. Only 2 female UC cases did not respond to CS therapy following an eight week treatment course. Repeat urine samples were collected from most patients, however samples were infrequently provided at later time periods. As a result, a repeat measures 2-way ANOVA was initially performed on a sub-set of IBD cases (UC-EEN, n=5; CD-CS, n=5) at baseline with matching urine samples collected at 2 and 4 weeks following the initiation of induction therapy. Table 6 highlights that 8 urinary metabolites showed significant interaction effects (treatment×time) between EEN and CS treatment arms with moderate (0.40-0.60) to large effect sizes (>0.70), notably an unknown anion tentatively identified (level 3) as octanoyl glucuronide based on its diagnostic MS/MS spectrum, as well as pantothenic acid and pyridoxic acid.

TABLE 6

A repeat measures 2-way ANOVA of sum-normalized log-transformed for monitoring changes in urine metabolome of pediatric IBD patients (n = 10) following EEN or CS induction therapy (0, 2, 4 weeks).

| m/z:RMT:mode | Metabolite ID; HMDB# | F-value | p-value | Effect size |
|---|---|---|---|---|
| 319.140:0.782:n | Octanoylglucuronide; HMDB0010347[a] | 32.0 | 2.55 E-06 | 0.800 |
| 218.103:0.836:n | Pantothenic acid; HMBD0000210 | 30.5 | 3.45 E-06 | 0.792 |
| 182.046:0.948:n | Pyridoxic acid; HMDB0000017 | 10.4 | 0.00127 | 0.566 |
| 212.002:1.025:n | Indoxyl sulfate; HMDB0000682[a] | 6.46 | 0.00877 | 0.447 |
| 191.066:1.007:p | Unknown; $C_6H_{10}N_2O_5$ | 6.31 | 0.00952 | 0.441 |
| 138.055:0.909:p | Trigonelline; HMDB0000875 | 5.74 | 0.0132 | 0.418 |
| 201.113:1.218:n | Sebacic acid; HMDB0000792[a] | 4.37 | 0.0307 | 0.353 |
| 308.078:1.302:n | Indoxyl glucuronide; [a] HMDB0010319 | 4.30 | 0.0320 | 0.350 |

* Statistical significance (p < 0.05) based on interaction term (treatment × time) for log-transformed urine metabolome data with effect size calculated using partial eta².
[a] Putative identification (level 3) of unknown metabolites based on accurate mass, MS/MS and mobility matching.

Figure 9:
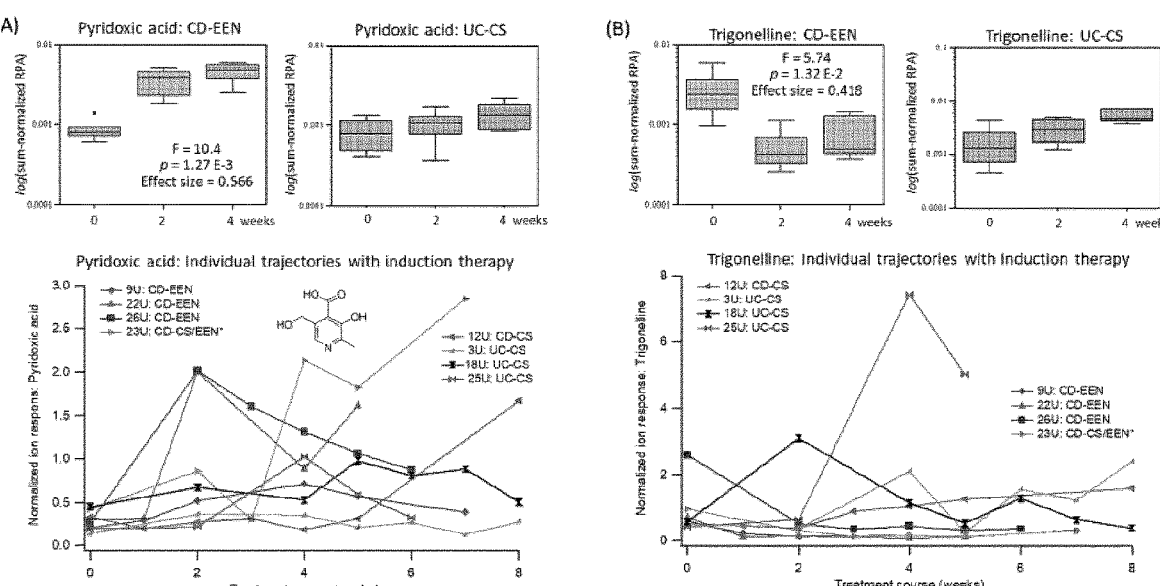
FIG. 9. Top-ranked urinary biomarkers associated with adherence to EEN among pediatric IBD children (n=10), namely (A) octanoylglucuronide and (B) pantothenic acid. Box-whisker plots show a specific elevation in the excretion

The latter B vitamins are key constituents of the EEN formula, whereas octanoyl glucuronide is a biotransformed metabolite from consumption of medium-chain triglycerides since coconut/palm kernel oil is used as the major source of dietary fat for IBD children. Urinary octanoyl glucuronide is also strongly correlated to pantothenic acid (r=0.772, n=97) and pyridoxic acid (r=0.767, n=97) and they are excreted progressively higher in IBD children prescribed EEN, but remain low and unchanged following CS therapy. FIG. 9 depicts box plots for urinary octanoyl glucuronide and pantothenic acid that have the most striking temporal changes following EEN therapy and have analogous levels at baseline for both CD and UC children. Urinary metabolite trajectories are also shown for individual IBD children (n=8) with samples collected up to 8 weeks, including a IBD patient who was initially prescribed with CS, but later was switched to EEN (>week 3) due to an ambiguous IBD diagnosis upon initial recruitment. Other urinary biomarkers reflecting adherence to EEN therapy identified in this study (Table 6) had less pronounced temporal changes especially when assessing their individual metabolic trajectories as compared to baseline and the CS treatment arm, such as pyridoxic acid and trigonelline, as well as indoxyl sulfate, sebacic acid, indoxyl glucuronide and an unknown cation (191.066:1.007:p; $C_6H_{10}N_2O_5$).

A differential analysis of urine metabolic phenotypes among IBD children following 4 weeks of induction therapy also revealed that CS therapy coincided with a progressive decrease in the excretion of several endogenous urinary steroid conjugates as compared to baseline and the EEN treatment arm, tentatively identified as cortolone glucuronide, hydroxyandrosterone glucuronide, tetrahydrocortisone glucuronide and an unknown steroid anion (525.269: 0.733:n). Nevertheless, mucosal healing likely takes place early during either CS or EEN treatment as reflected by progressively lower serum CRP and FCP concentrations evident in IBD children within 4 weeks of treatment initiation. A correlation matrix summarizing the relationship among the 21 urinary metabolites identified as differentiating biomarkers of pediatric IBD in this study, as well as specific treatment responses to EEN or CS therapy together with conventional biomarkers of systemic/colonic inflammation (CRP, FCP) was prepared. Overall, six distinct clusters of urinary metabolites are evident suggesting a common regulatory pathway and/or origin, including hydroxylated amino acids (serine, threonine), endogenous steroid glucuronides putatively modulated by oral prednisone, exogenous/biotransformed nutrients from dietary intake of EEN, uremic toxins likely reflecting differences in gut microbiota composition, and energetic/oxidative stress metabolites (hypoxanthine, unknown cation: 222.078:0.849: p). Overall, sialic acid was the only urinary metabolite (p<0.05) correlated with FCP (r=0.386) and CRP (r=0.216) from pediatric IBD patients, whereas urinary hypoxanthine was modestly associated only with FCP (r=0.307).

DISCUSSION

Differentiation of CD from UC based on metabolic phenotyping has proven elusive largely due to the clinical heterogeneity of adult IBD, and the confounding effects of long-term maintenance medications and surgeries on host metabolism and gut microbiome. Therefore, this study focused on newly diagnosed pediatric IBD cases, with most children being treatment naïve while in an active disease state prior to introducing two contrasting induction therapies (Table 4), as there still remains no effective cure.

In this work, urine metabolomic analyses was performed using a validated data workflow for authenticating a diverse range of polar/hydrophilic metabolites by MSI-CE-MS with minimal sample workup and stringent quality control. Sum or osmolality normalization of single-spot urine samples provided consistent outcomes for urinary biomarkers associated with IBD sub-types and their treatment responses to induction therapy. This was needed to adjust for variations in hydration status since creatinine is not optimal for young children and adolescents having different muscle mass while also undergoing changes in habitual diet. In this work, it was discovered that children with CD have higher excretion of indoxyl sulfate and a novel urinary metabolite identified by MS/MS for the first time as 5-hydroxyindoxyl-3-O-sulfate, along with corresponding lower kynurenine as compared to age/sex-matched UC cases (Table 5). Elevated levels of indoxyl sulfate and other indole/aryl metabolites (e.g., indoxyl glucuronide, phenylacetylglutamine, cresol sulfate)

can function as uremic toxins in circulation to promote oxidative stress in end-stage chronic kidney disease, which may also contribute to epithelial barrier injury among IBD patients who otherwise have normal kidney function yet suffer from underlying gut dysbiosis. In contrast, increased tryptophan catabolism via the kynurenine pathway is associated with greater endoscopic mucosal inflammation that is predictive of disease outcomes in UC patients.

Differential excretion of two hydroxylated amino acids, namely serine and threonine, was found in the urine of UC as compared to CD children. In fact, threonine and serine have promising therapeutic properties for treatment of IBD since they are limiting amino acids during active inflammation as they are required for mucin synthesis to promote colonic protection and mucosal healing. Also, urinary sialic acid is excreted higher in CD as compared to UC children reflecting differences in IBD pathophysiology and gut dysbiosis (Table 5) while also being correlated with FCP serum and CRP as independent indicators of inflammation attenuated in most patients following induction therapy. Also, hypoxanthine was higher in the urine of UC as compared to CD patients. Urinary hypoxanthine is also positively correlated to FCP suggesting that a common motif of energetic/oxidative stress is more pronounced in UC as compared to colonic inflammation in CD. Furthermore, phenylacetylglutamine was excreted higher in CD as compared to UC children. Two unknown urinary metabolites also differentiate CD from UC children, which are tentatively identified by MS/MS as a dicarboxylic acid analog (345.155:0.777:n, $C_{16}H_{26}O_8$), and a sulfur amino acid conjugate (222.080: 0.849:p, $C_8H_{15}NO_4S$) correlated to hypoxanthine (r=0.566). Overall, the ratio of serine:hydroxyindoxyl sulfate or serine: indoxylsulfate provide excellent accuracy (AUC~0.965) for discriminating between the two major IBD subtypes in recently diagnosed children unlike FCP or CRP. Furthermore, stability studies confirmed that most metabolites identified in this study can be reliably measured upon refrigeration of urine for up to 2 days without the need for sodium azide as a preservative additive.

Since metabolic profiles, especially that of urine, tend to be strongly influenced by changes in habitual diet in healthy populations or following specific dietary restrictions for treatment of rare metabolic disorders, one of challenges in this study was to distinguish metabolites/nutrients directly associated with intake of EEN formula from downstream changes in host/gut microflora metabolism coinciding with clinical remission. As expected, initiation of EEN therapy constitutes a drastic change in normal oral feeding patterns in children from baseline as it is comprised of a liquid formula delivered via nasogastric tubing to meet total caloric and nutritional demands, which was mainly prescribed to CD children with active inflammation over an eight week period. Several clinical studies to date have shown that EEN is most effective when used as the first-line treatment in pediatric CD with clinical remission rates of about 73-80% that induces mucosal healing superior to conventional CS therapy without adverse effects on growth; however, it suffers from lower efficacy with repeated treatments, In the present study, 72% of recently diagnosed CD children (as well as one UC patient, n=19) were prescribed EEN for the first time, and most patients achieved full remission (~68%) or a positive treatment response with a lower disease activity score or inflammation (~32%) from baseline after 8 weeks. Urinary octanoyl glucuronide was identified as the most specific and robust biomarker for monitoring of adherence to EEN (Table 6) that significantly increases within 1 week of feeding with a median 15.5-fold increase at 4 weeks as compared to baseline (FIG. 9A). Metabolic trajectories for urinary octanoyl glucuronide also demonstrated good sensitivity and specificity to detect a delayed introduction of EEN in one patient (23U) after week 3 who was initially prescribed CS therapy due to an ambiguous diagnosis. Additionally, urinary pantothenic acid (vitamin B5) and pyridoxic acid (catabolite from pyridoxine or vitamin B6) were also elevated among IBD patients following EEN as compared to their baseline and the CS treatment arm (FIG. 9) with a strong interaction (treatment×time) effect size (Table 6 albeit to a lesser extent than octanoyl glucuronide.

Urinary trigonelline, a methylated catabolite of niacin, was also found modestly responsive to EEN therapy (Table 6), however it was less significant than other B vitamins since it is also enriched in commonly consumed foods (e.g., wheat flour) in most developed countries unlike pyridoxine and pantothenic acid. As a result, specific macro- and micronutrients (and their biotransformed metabolites in urine) prevalent in EEN formulations as compared to habitual Western diets, offer a convenient way to monitor dietary adherence in children, as well as their improved nutritional status to support normal growth and mucosal healing.

In summary, nontargeted metabolite profiling of urine samples from pediatric IBD patients has identified a panel of discriminating metabolites that offers a simple way to differentiate CD from UC children and reduce the need for repeat colonoscopies for ambiguous or treatment nonresponsive cases. Also, other urinary metabolites may serve as useful biomarkers for treatment monitoring of efficacious EEN therapies to induce clinical remission, including dietary adherence and nutritional repletion of CD children who are prone to vitamin deficiencies. Most urinary biomarkers can be reliably measured in a clinical setting while tolerating delays to freezing without preservatives if refrigerated. Rigorous metabolomics data workflow was applied to reduce false discoveries that was applied in a longitudinal clinical intervention trial involving two contrasting therapeutic treatments for inducing remission in IBD children.

The invention claimed is:

1. A method of differentiating between UC and CD in a subject comprising:
   i) detecting in a urine sample from the subject the level of at least two metabolic biomarkers selected from the group consisting of serine, hypoxanthine, kynurenine, threonine, indoxylsulfate, phenylacetylglutamine, 5-hydroxy-6-indolyl-O-sulfate, 5-(δ-carboxybutyl) homocysteine, sialic acid and an anion having m/z: RMT:polarity of 345.1553:0.770:n;
   ii) comparing the level of the detected biomarkers to a standard, UC or CD control level and determining the difference between the biomarker level and the selected control level;
   iii) a) determining that the subject has UC when the level of serine, hypoxanthine, kynurenine, and threonine exhibit is statistically greater than the standard or CD control level or the level of indoxylsulfate, phenylacetylglutamine, 5-hydroxy-6-indolyl-O-sulfate, 5-(δ-carboxybutyl) homocysteine, sialic acid and an anion having m/z:RMT:polarity of 345.1553:0.770:n is statistically less than the standard or CD control level, or
   b) determining that the subject has CD when the levels of indoxylsulfate, phenylacetylglutamine, 5-hydroxy-6-indolyl-O-sulfate, 5-(δ-carboxybutyl) homocysteine, sialic acid, and an anion having m/z:

RMT:polarity of 345.1553:0.770:n is statistically greater than the UC control level, or the level of serine, hypoxanthine, kynurenine, and threonine is statistically less than the standard UC control level; and
   iv) optionally, treating the subject with one or more of an anti-inflammatory, corticosteroid, antibiotic, biologic, immunomodulatory, modified diet and surgery.

2. The method of claim 1, wherein at least two of serine, threonine and indoxylsulfate are detected.

3. A method of diagnosing UC in a subject comprising:
   i) detecting in a urine sample from the subject the level of at least two metabolic biomarkers selected from the group consisting of serine, hypoxanthine, kynurenine and threonine;
   ii) comparing the level of the detected biomarkers to a standard control level and determining the difference between the biomarker level and the selected control level; and
   iii) determining that the subject has UC when the level of selected biomarkers is statistically greater than the standard control level.

4. The method of claim 3, comprising the additional step of detecting the level of one or more biomarkers selected from serine, tryptophan, choline, hypoxanthine and lactic acid in a stool sample, wherein an increased level of the one or more biomarkers as compared to a control level is indicative of UC.

5. A method of diagnosing CD in a subject comprising:
   i) detecting in a urine sample from the subject the level of at least two metabolic biomarkers selected from the of indoxylsulfate, 5-hydroxy-6-indolyl-O-sulfate, phenylacetylglutamine, 5-(δ-carboxybutyl) homocysteine, sialic acid or an anion having m/z:RMT:polarity of 345.1553:0.770:n;
   ii) comparing the level of the detected biomarkers to a standard control level and determining the difference between the biomarker level and the selected control level; and
   iii) determining that the subject has CD when the level of selected biomarkers is statistically greater than the standard control level.

6. The method of claim 1, wherein the at least two biomarkers are selected from serine and indoxylsulfate; threonine and phenlylacetylglutamine; serine and phenylacetylglutamine; and tryptophan and indoxylsulfate; are detected, and their ratio is used to differentiate between UC and CD.

7. The method of claim 6, comprising the additional step of detecting the level of one or more biomarkers selected from ketodeoxycholic acid, cholic acid, trimethyllysine, butyric acid and guanine in a stool sample, wherein an increased level of the one or more biomarkers as compared to a control level is indicative of CD.

8. The method of claim 6, wherein serine and indoxylsulfate are detected.

9. The method of any one of claims 1-2 and 3-8, wherein the subject is a pediatric patient.

10. The method of any one of claims 1-2 and 3-8, wherein the biomarkers are detected using a mass spectrometry-based method.

11. The method of any one of claims 1-2 and 3-8, wherein the biomarkers are detected using an immunoassay.

* * * * *